United States Patent [19]
Midoux et al.

[11] Patent Number: 5,595,897
[45] Date of Patent: Jan. 21, 1997

[54] POLYLYSINE CONJUGATES

[75] Inventors: Patrick Midoux; Patrick Erbacher, both of Orleans; Annie-Claude Roche-Degremont, Sandillon; Michel Monsigny, Saint-Cyr-en-Val, all of France

[73] Assignee: I.D.M. Immuno-Designed Molecules, France

[21] Appl. No.: 288,681

[22] Filed: Aug. 10, 1994

[30] Foreign Application Priority Data

Apr. 28, 1994 [FR] France ................................. 94 05174

[51] Int. Cl.⁶ .......................... C07K 1/00; C07K 1/107; C12N 15/00; C12N 15/88
[52] U.S. Cl. ...................... 435/172.3; 435/6; 435/69.1; 435/183; 435/189; 435/193; 435/194; 435/207; 435/240.2; 435/320.1; 530/300; 530/345; 530/350; 530/402
[58] Field of Search .......................... 435/172.1, 172.3, 435/6, 69.1, 91.1, 320, 240.1, 240.2, 183, 189, 193, 194, 207; 530/345, 395, 402, 300, 350; 536/23.1, 23.2, 23.5, 23.7, 23.72, 23.74; 514/44

[56] References Cited

PUBLICATIONS

Crystal "Transfer of Genes to Humans: Early Lessons and Obstacles" Science 270:404–410 Oct. 1995.
Gura "Antisense has Growing Pains" Science 270:575–577 Oct. 1995.
Kabanov et al. "DNA Complexes with Polycations for the Delivery of Genetic Material into Cells" Bioconjugate Chem. 6:7–20 1995.

*Primary Examiner*—John L. LeGuyader
*Assistant Examiner*—Thomas G. Larson
*Attorney, Agent, or Firm*—Bierman & Muserlian

[57] ABSTRACT

The invention concerns a complex between at least one negatively charged nucleic acid and at least one positively charged polymeric conjugate, the link between the nucleic acid and the polymeric conjugate being electrostatic in nature, the polymeric conjugate containing a polymer formed from monomer components having free $NH_3^+$ functions of the aforementioned components and being as follows:

—the free $NH_3^+$ functions from the aforementioned components are substituted in a ratio of at least 10%, advantageously from 45% to 70%, particularly 60%, by noncharged residues leading to a reduction of positive charges in comparison to the same nonsubstituted polymeric conjugate, facilitating the release of nucleic acid by the dissociation of the complex, —the aforementioned residues possess in addition the following properties:
  →they contain at least one hydroxyl group,
  →they do not correspond to a recognition signal recognized by a cellular membrane receptor, —the free $NH_3^+$ functions from the above mentioned components and/or the hydroxyl groups of the above mentioned residues are also able to be substituted by at least one molecule which constitutes a recognition signal recognized by a cellular membrane receptor, under the condition that the polymeric conjugate contains at least 30% free $NH_3^+$ functions.

9 Claims, 9 Drawing Sheets

POLYLYSINE CONJUGATES

The introduction of a foreign gene in a cell is of great interest for gene therapy. While in in vitro experiments, general methods using calcium phosphate precipitation, DEAE dextran, or cationic lipids are suitable, more selective methods are required to specifically transfer a gene into a given cell population with the aim of developing gene therapy. Amongst these selective methods, gene transfer may be achieved by making use either of modified virus material starting with vaccinia virus or retrovirus, or of targeted liposomes, or of targeted macromolecule gene complexes. DNA/carrier complexes such as polylysine substituted with asialoorosomucoide, insulin or transferrine have been proposed as targeted carriers of plasmid allowing cell transfection upon an endocytotic process induced by the corresponding receptors: the galactose specific receptor (lectin) with the asialoorosomucoide, the insulin receptor and the transferrin receptor.

It has been established that numerous animal cells possess membrane lectins [Monsigny M., Roche A. C., Kieda C., Midoux P., Obrenovitch A. Characterization and biological implications of membrane lectins in tumor, lymphoid and myeloid cells. Biochimie, 1988: 70: 1633–49; Varki A. Selectin and other mammalian sialic acid binding lectins. Curr. Op. in Cell. Biol., 1992, 4: 257–66] which specifically recognize the osides of various structures. In particular, the membrane lectin of cells of the hepatic parenchyma cells recognize oligosaccharides with a galactose residue in terminal nonreducing position, which means that all galactose has alcohol functions free, as is the case of asiolo-glycoproteins [Ashwell G., Harford J. Carbohydrate-specific receptors of the liver. Ann. Rev. Biochem., 1982, 51: 531–54].

The specificity of these lectins depends on the cell type, and therefore membrane lectins are good candidates for gene transfer by glycoconjugate/DNA complexes as specific carriers. Soluble glycoconjugates bearing defined sugar moieties have been used to efficiently target drugs, including cytotoxic drugs, toxins, immunomodulators, antiviral drugs [see, Monsigny M., Roche A. C., Kieda C., Midoux P. and Obrenovitch A. Biochemie, 1988: 70:1633–49 2; Roche A.C., Midoux P., Pimpaneau V., Nègre E., ayer R. and Monsigny M. Res. Virol., 1990: 141: 243–249] and oligonucleotides [Bonfils E., Depierreux C., Midoux P., Thuong N. T., Monsigny M., Roche A.C. Drug targeting: synthesis and endocytosis of oligonucleotide-neoglycoprotein conjugates. Nucleic Acids Res., 1992, 20: 4621–9; Bonfils E., Mendès C., Roche A.C., Monsigny M., Midoux P. Uptake by macrophages of a biotinylated oligo-a-deoxythymidylate by using mannosylated streptavidin. Bioconjuguate Chem., 1992, 3: 277–84].

Plasmid associated macromolecules capable of being specifically recognized by plasma membrane components of cell targets enter cells by a process mimicking the mechanism of entry of viral genetic material into cells. In every case described up to now, the macromolecular plasmid-carrier complex is specifically recognized by a membrane receptor which pulls the complex into intracellular vesicle endosomes by endocytosis, and probably into other deeper intracellular compartments, far from the plasma membrane.

Moreover, the transmembrane passage of plasmid DNA is a critical process for its delivery into the cytosol and/or the nucleus, where the gene will be expressed.

The invention is of new stable complexes of nucleic acid and of substituted polymer.

The invention also is of new complexes of nucleic acid and substituted polymers which are able, upon dissociation, to release nucleic acid, in order to allow an effective expression of transfected nucleic acid into the cells.

The invention is of new nucleic acid complexes and substituted polymer which do not contain any recognition signals and which are able to transfect several types of cells.

The invention is of new nucleic acid complexes and substituted polymer which contain recognition signals recognized by membrane receptors, making the transfection selective for different types of cells.

The invention is of a method of specific cell transfection in vitro or in vivo.

The invention also is of new conjugates of polylysine capable of being linked to a nucleic acid in preparation for the selective transfection of a cell.

The invention is also of new pharmaceutical compositions containing, as an active component, a complex of DNA and substituted polymers, particularly of substituted polylysine.

The invention is also of new complexes of nucleic acid and of substituted polymer possessing a high solubility in physiologic serum and divers culture mediums, capable of being administered in vivo at very high dosage levels.

The invention, in one of its most general definitions, concerns a complex between at least one negatively charged nucleic acid and at least one positively charged polymeric conjugate, the association between the nucleic acid and the polymeric conjugate being electrostatic in nature, the polymeric conjugate containing monomeric components harboring $NH_3^+$ free functions of the above mentioned components, and being as follows:

— the free $NH_3^+$ functions of the aforementioned components are substituted in a ratio of at least 10%, advantageously from 45% to 70%, particularly by 60%, by non-charged residues leading to a reduction of the number of positive charges in comparison with the same non-substituted polymeric conjugate, facilitating the release of nucleic acid by the dissociation of the complex, — the aforementioned residues possess in addition the following properties:

→ they contain at least one hydroxyl group,

→ they do not correspond to a recognition signal recognized by a cellular membrane receptor, — the free $NH_3^+$ functions of the aforementioned components and/or the hydroxyl groups from the aforementioned residues are also able to be substituted by a molecule which constitutes a recognition signal recognized by a cellular membrane receptor, under the condition that the polymeric conjugate, after substitution by the aforementioned residues and by the aforementioned recognition signals, contains at least 30% free $NH_3^+$ functions.

The originality of the invention is based on the use of a substituted polymer by a sufficient quantity of residues, allowing, i) the formation of stable complexes with a nucleic acid, polynucleotides RNA or DNA, particularly DNA, by electrostatic interactions between the negative charges of the nucleic acid, particularly DNA, and the remaining positive charges of the partially substituted polymer with the afore mentioned residues, and ii) the facilitation of the dissociation of the complex and the release of the nucleic acid in order to allow an efficient expression of the gene in the transfected cells.

Indeed, the aforementioned substituted polymer allows a condensation of the DNA which remains very strong as a result of a cooperative phenomenon between the positive charges of the polymer and the negative charges of the DNA. For example, the substituted polymer at 58% with an aforementioned residue possesses less positive charges, which thus reduces the interaction cooperativity and facilitates the dissociation between the DNA and the polymer.

The dissociation of the complex can be measured under the conditions described under FIG. 6.

Taken by itself, the polymeric conjugate contains monomers which harbor $NH_2$ free functions which are capable of becoming $NH_3^+$ under appropriate pH conditions (pH <10).

Furthermore, the presence of a cellular membrane recognition signal is not required.

The expression according to which "the residues substituting $NH_2$ do not correspond to any cellular membrane recognition signal" means that they do not correspond to any signal according to what is known today in the literature.

By recognition signal recognized by a cellular membrane receptor, we generally mean a molecule or a molecular complex able to selectively recognize a ligand (signal-receptor affinity $\geq 10^3$ 1/mole).

The number of recognition signals which substitute the free $NH_3^+$ of the aforementioned components and/or the hydroxyl groups of the aforementioned residues varies from 0 to 40%.

Given that the number of free $NH_3^+$ on the polymeric conjugate must be at least 30%, while the $NH_3^+$ of the aforementioned components are substituted by 10% of non-charged residues, particularly gluconoyle, the number of recognition signals may be up to 40% of the 90% non-engaged $NH_3^+$ with non-charged residues and/or on the hydroxyl groups of the aforementioned residues. While 45% of the $NH_3^+$ of the aforementioned components are substituted by 45% with non-charged residues, the recognition signals are able to be on 25 of the 55% of $NH_3^+$ which are not substituted with the non-charged residues and/or on the hydroxyls of the aforementioned residues. On the other hand, while the number of $NH_3^+$ engaged in links with the residues increases up to 70%, with the result that the polymeric conjugate keeps at least 30% of free $NH_3^+$, the recognition signals are no longer able to exist except when they substitute the hydroxyls of the aforementioned residues.

The invention particularly concerns a complex between at least one negatively charged nucleic acid and at least one positively charged polymeric conjugate, the association between the nucleic acid and the polymeric conjugate being electrostatic in nature, the polymeric conjugate containing a polymer formed by monomeric components harboring free $NH_3^+$ functions of the aforementioned components, and being as follows:

— the free $NH_3^+$ functions of the aforementioned components are substituted in a ratio of at least 10%, advantageously from 45% to 70%, particularly 60%, with non-charged residues leading to a reduction of positive charges in comparison with the same non-substituted polymeric conjugate, facilitating the release of the nucleic acid by dissociation from the complex;

— the aforementioned residues possess, in addition, the following properties:
→they contain at least one hydroxyl group,
→they do not correspond to a recognition signal recognized by a cellular membrane receptor, — the free $NH_3^+$ functions of the aforementioned components of the said residues are also able to be substituted with at least one molecule which constitutes a recognition signal recognized by a cellular membrane receptor, under the condition that the polymeric conjugate contains at least 30% free $NH_3^+$ functions.

The invention particularly concerns a complex between at least one negatively charged nucleic acid and at least one positively charged polymeric conjugate, the association between the nucleic acid and the polymeric conjugate being electrostatic in nature, the polymeric conjugate containing a polymer formed by monomeric components harboring free $NH_3^+$ functions of the aforementioned components and being as follows:

— the free $NH_3^+$ functions of the aforementioned components are substituted in a ratio of at least 10%, more effectively from 45% to 70%, particularly by 60%, by noncharged residues leading to a reduction of positive charges in comparison with the same non-substituted polymeric conjugate, facilitating the release of the nucleic acid by dissociation from the complex, — the aforementioned residues possess, in addition, the following properties:
→ they contain at least one hydroxyl group,
→ they do not correspond to a recognition signal recognized by a cellular membrane receptor, — the hydroxyl groups of the aforementioned residues are able to be substituted with at least one molecule which constitutes a recognition signal recognized by a cell membrane receptor, under the condition that the polymeric conjugate contains at least 30% free $NH_3^+$ functions.

In accordance with an advantageous embodiment, the invention concerns a complex between at least one negatively charged nucleic acid and at least one positively charged polymeric conjugate, the association between the nucleic acid and the polymeric conjugate being electrostatic in nature, the polymeric conjugate containing a polymer formed from monomeric components which possess free $NH_3^+$ functions, in particular residues of lysine, and being as follows:

— the free $NH_3^+$ functions of the aforementioned components are substituted in a ratio of at least 10%, advantageously from 45% to 70%, particularly by approximately 60%, with non-charged residues leading to a reduction of positive charges in comparison with the same non-substituted polymeric conjugate, thus facilitating the dissociation of the complex and the release of the nucleic acid, — the aforementioned residues possess, in addition, the following properties:
→ they contain at least one hydroxyl group,
→ they do not correspond to a cell recognition signal,
—0 to 40% of the number of free $NH_3^+$ functions of the above mentioned components being also substituted by a molecule which constitutes a recognition signal recognized by a cellular membrane receptor, this recognition signal having a molecular mass less than 5,000, under the condition that the polymeric conjugate comains at least 30% free $NH_3^+$ functions, and when it is present, this recognition signal can exist at the ratio of one molecule for approximately 10,000 components of the polymeric conjugate or approximately 60 molecules for approximately 10,000 components of the polymeric conjugate.

The invention concerns more particularly a complex between at least one negatively charged nucleic acid and at least one positively charged polymeric conjugate, the association between the nucleic acid and the polymeric conjugate being electrostatic in nature, the polymeric conjugate containing a polymer formed by monomeric components which have free $NH_3^+$ functions, in particular residues of lysine and being as follows:

— the free $NH_3^+$ functions of the aforementioned components are substituted in a ratio of at least 10%, advantageously from 45% to 70%, particularly by approximately 60%, with non-charged residues leading to a reduction of positive charges in comparison with the same non-substituted polymeric conjugate, thus facilitating the dissociation of the complex and the release of the nucleic acid, — the aforementioned residues possess, in addition, the following properties:

→ they contain at least one hydroxyl group,

→ they do not correspond to a cellular membrane recognition signal,

— the free $NH_3^+$ functions of the aforementioned components are able to be equally substituted by one molecule which constitutes a cellular recognition signal, this recognition signal being of molecular mass less than 5,000, and when it is present, this recognition signal can exist at the ratio of one molecule for approximately 10,000 components of the polymeric conjugate or approximately 60 molecules for approximately 10,000 components of the polymeric conjugate.

Under these conditions, taking into account the low number of recognition signals, at least 30% of the $NH_3^+$ of the polymeric conjugate are free.

When they are present, the purpose of the recognition signals is to render selective the transfection with regards to the nature of different types of cells and to make the transfection effective in vivo.

The recognition signals, taking into account the fact they generally are neutral, also have the effect of leading to a decrease of positive charges in the polymeric conjugate.

The recognition signals are molecules of low molecular mass (<5,000 daltons).

The number of recognition signal molecules fixed on the modified polymer can be, — for a signal molecule with a very high affinity in relation to its receptor, from 0.5 to 5, advantageously 1 molecule for approximately 10,000 monomeric components of substituted polymer, thus being 1 molecule for approximately 50 molecules of substituted polymer;

— for a signal molecule with medium affinity in relation to its receptor, approximately 10 to 100, advantageously 50 molecules for approximately 10,000 monomeric components of substituted polymer.

A signal molecule of very high affinity corresponds to Ka value of at least $10^6$ 1/mole.

A signal molecule of medium affinity corresponds to a Ka value of at least $10^4$ 1/mole.

In accordance with an advantageous embodiment, in the complexes of the invention, the polymer contains a polymeric group of the following formula (I):

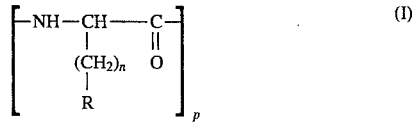

in which:

—p is an integer varying from 2 to 500, preferably from 150 to 200,

—n is an integer varying from 1 to 5 and being preferably 4,

—this polymeric group contains a number of p of R residues among which:

* 10% to 70% of the number of R residues represents a NH—CO—$(CHOH)_m$—$R_1$ group, particularly a dihydroxylpropionoyle, erythrononoyle, threonoyle, ribonoyle, arabinoyle, xylonoyle, lyxonoyle, gluconoyle, galactonoyle, mannonoyle, glycoheptonoyle, glycooctonoyle residue, — m is an integer from 2 to 15, preferably from 2 to 7, — $R_1$ represents H or an alkyl residue from 1 to 15 carbon atoms, particularly $CH_3$,

* the remaining residues, which are the 30% to 90% of the number of R residues, represent $NH_3^+$,

* R, moreover, having the ability to be constituted in 0 to 25% of the cases by a molecule which constitutes a recognition signal, under the condition that the polymeric conjugate contains at least 30% free $NH_3^+$ functions, and particularly at the ratio of 0.5 to 5, advantageously at 1 molecule for approximately 10,000 components, or at the ratio of 10 to 100, advantageously at 60 molecules for approximately 10,000 components.

In accordance with an advantageous embodiment, the invention concerns a complex as defined previously, in which the polymer includes a polymeric group of formula (II):

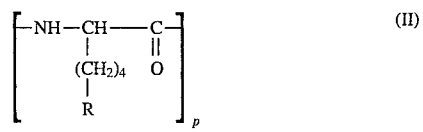

in which:

—p has the meanings indicated above,

* 10% to 70% of the number of R residues represents a NH—CO—$(CHOH)_m$—$R_1$ group, m and $R_1$ having the meanings indicated above,

* the remaining residues, which are the 30% to 90% of the number of R residues, represent $NH_3^+$, and between 0 to 25% of the R residues are able to be substituted by a molecule which constitutes a recognition signal recognized by a cellular membrane receptor, under the condition that the polymeric conjugate contains at least 30% free $NH_3^+$ functions.

According to another embodiment, in the complexes of the invention, the polymer includes a polymeric group of formula (II):

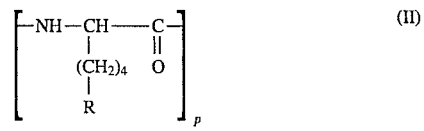

in which:

—p has the meanings indicated above,

* 10% to 70% of the number of R residues represent a NH—CO—$(CHOH)_m$—$R_1$ group, m and $R_1$ having the meanings indicated above,

* the remaining residues, which are the 30% to 90% of the number of R residues, represent $NH_3^+$.

In this class of complexes of the invention, the polymer is a polylysine.

As demonstrated in the examples, HepG2 (human hepatocarcinoma) cells are efficiently transfected by the substituted polylysine containing 58±12% (110±22 residues) gluconoyle residues with an efficiency approximately 300 times higher than with the plasmid alone. The polylysines substituted by a few gluconoyle residues are not effective for obtaining a good transfection; those substituted by too many residues are slightly effective for obtaining a good transfection.

The polylysine substituted with 58±12% gluconoyle residues has the ability to transfect different cells adhering or in suspension (from humans, mice, rats, rabbits, monkeys, etc.) with a great efficacy, modulated according to the cell type and the promoter used.

According to another advantageous embodiment, in the complexes of the invention, the polymer comprises a polymeric group of formula (II):

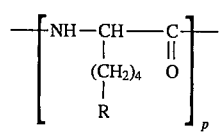  (II)

in which:
— p has the meanings indicated above,
— this polymer contains a number p of R residues among which:
 * 10% to 70% of the number of R residues represents a NH—CO—(CHOH)$_m$—R$_1$ group, m and R$_1$ having the meanings indicated above,
 * the remaining residues, which are the 30% to 90% of R residues, represent in one part NH$_3^+$ and, in another part, represent a molecule which constitutes a recognition signal at the ratio of 0.5 to 5, advantageously at 1 molecule for 10,000 components.

According to another embodiment, in the complexes of the invention, the polymer comprises a polymeric group of formula (II):

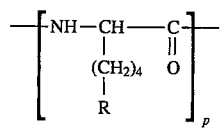  (II)

in which:
— p has the meanings indicated above,
— this polymer contains a number p of R residues among which:
 * 10% to 70% of the number of R residues represents a NH—CO—(CHOH)$_m$—R$_1$ group, m and R$_1$ having the meanings indicated above,
 * the remaining residues, which are the 30% to 90% of the number of R residues, represent in one part NH$_3^+$ and, in another part, represent a molecule which constitutes a recognition signal at the ratio of 10 to 100, advantageously at 60 molecules for approximately 10,000 components.

In the complexes of the invention, the recognition signal could be chosen from the following:

A) —from simple or complex osides recognized by membrane lectins, and chosen among the following items:

a. Asialo-oligoside of triantennary lactosamin type: assialoglycoprotein receptor

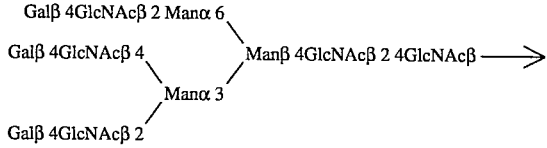

b. Asialo oligoside of tetraantennary lactosamin type: assialoglycoprotein receptor

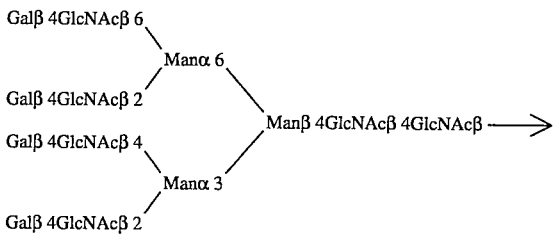

c. Lewis x: LECAM 2/3

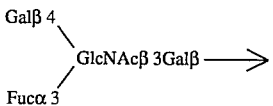

d. Sialyl Lewis x: LECAM 3/2

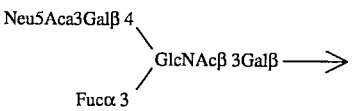

e. Sulfated Lewis x (HNK1): LECAM 1

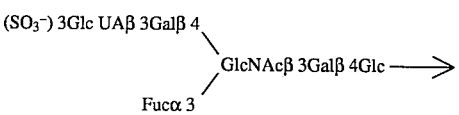

-continued f. Oligomannoside: mannose receptor

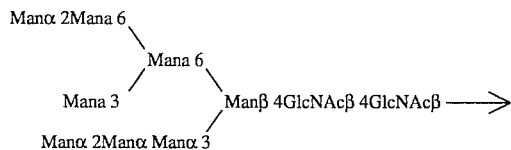

g. Phosphorylated oligomannoside: mannose 6 phosphate receptor

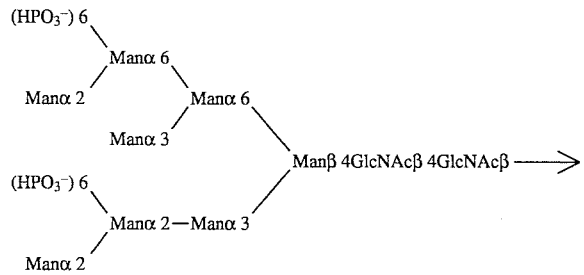

h. Sulfated oligosaccharide of lactosamin type: sulfated GalNAc 4 receptor

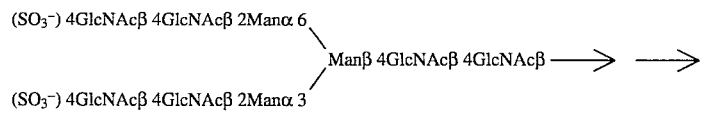

B) from peptides
  a) anti-inflammatory peptides or certain of their fragments recognized by the vascular cells, such as for example:
    —intestinal vasodilator polypeptide (IPV)
    HSDAVFTDNYTRLRKQMAVKKYLNSILN-NH$_2$ (SEQ ID NO:1)
    —natriuretic atrial polypeptide (NAP)
    SLRRSSCFGGRMDRIGAQSGLGCNSFRY (SEQ ID NO:2)
    —lipocortine
    HDMNKVLDL (SEQ ID NO:3)
    —bradykinine
    RPPGFSPFR (SEQ ID NO:4);
  b) peptide ligands of various integrines, such as peptides containing the sequence RGD (SEQ ID NO:5) recognized by the receptor of the fibronectine, for instance;
  c) chemotactic factors, such as formyl peptides and antagonists: FMLP, (N-formyl-Met-Leu-Phe);(SEQ ID NO:6)
  d) peptide hormones such as
    a-MSH: Ac-SYSMEHFRWGKPV-NH$_2$, (SEQ ID NO:7) for instance,
  C) Natural metabolites such as
    —biotine,
    — tetrahydrofolate,
    — folic acid,
    — carnitine.
    In the complexes of the invention, the nucleic acid is can be chosen among the following items:
  a) gene markers, such as
    — luciferase gene,
    —β-galactosidase gene,
    — chloramphenicol acetyl transferase gene,
    — genes bestowing the resistance to an antibiotic, such as hygromycine or neomycine,
  b) genes for therapeutic purposes, such as gene encoding
    —low density lipoprotein receptors, deficient in the case of hypercholesterolomia (liver),
    —coagulation factors: factors VIII and IX,
    —phenylalanine-hydroxylase (phenylcetonuria)
    —adenosine desaminase (ADA immunodeficiency)
    —lysosomic enzymes, such as β-glucosidase in the case of Gaucher's disease,
    —dystrophine and minidistriphine (myopathy)
    —tyrosine hydroxylase (Parkinson),
    —neurone growth factors (Alzheimer),
    —CFTR cystic fibrosis transmembrane conductance regulator (mucoviscidose),
    —alpha1-antitrypsine,
    —nuclear factors: NF-KB, CII TA, . . .
    —cytokines and interleukines, TNF: tumor necrosis factor,
    —thymidine kinase of the Herpes simplex virus,
    —MHC proteins, major histocompatibility system, in particular HLA-B7,
    —antioncogenes: p53, RB
    —cytosine desaminase,
    —sense and anti-sense RNA,
    —ribozymes,
  c) genes with vaccine purposes: genes encoding
    —viral antigens, for example, the nucleoprotein of the influenza virus.

One advantageous class of complexes in the invention consists of complexes in which:
  — the polymer, particularly polylysine, presents a degree of polymerization of approximately 100 to approximately 500, preferably 190,
  — the free NH$_3{}^+$ functions of the lysine components are substituted up to 60% with gluconoyle groups and possibly by a molecule constituting a recognition signal for 10,000 lysine residues when the said recognition signal possesses an affinity equal or higher than $10^6$ 1 mole$^{-1}$ in relation to the receptor of the cell which the complex should target, or possibly by 60 recognition signal molecules for 10,000 lysine residues when the said recognition signal possesses an affinity equal or higher than $10^4$ 1 mole$^{-1}$ in relation to the aforementioned receptor, — the nucleic acid has a molecular mass of approximately $6.10^5$ to approximately $25.10^6$, and — the ratio between the mean number of base pairs of nucleic acid to the number of monomeric components of the polymer, particularly the lysine, is approximately 0.9 to approximately 1.1, preferably approximately 0.95 to approximately 1.05.

The invention also concerns a positively charged polymeric conjugate, the association between the nucleic acid and the polymeric conjugate being electrostatic in nature, the polymeric conjugate containing a polymer formed by monomeric components having free $NH_3^+$ functions of the aforementioned components and being as follows:

— the free $NH_3^+$ functions of the aforementioned components are substituted in a ratio of at least 10%, advantageously by 45% to 70%, particularly by 60%, with noncharged residues leading to a reduction of positive charges in comparison with the same non-substituted polymeric conjugate, facilitating the release of nucleic acid by dissociation of the complex, — the aforementioned residues possess in addition the following properties:

→ they contain at least one hydroxyl group,

→ they do not correspond to a recognition signal recognized by a cellular membrane receptor, — the free $NH_3^+$ functions of the aforementioned components and/or the hydroxyl groups of the aforementioned residues may also be substituted with at least one molecule which constitutes a recognition signal recognized by a cellular membrane receptor, under the condition that the polymeric conjugate contains at least 30% free $NH_3^+$ functions.

This polymeric conjugate is an intermediate component of the previously described complexes.

In accordance with an advantageous embodiment, the invention concerns a positively charged polymeric conjugate, the association between the nucleic acid and the polymeric conjugate being electrostatic in nature, the polymeric conjugate containing a polymer formed by monomeric components having free $NH_3^+$ functions and being as follows:

— the free $NH_3^+$ functions of the aforementioned components are substituted in a ratio of at least 10%, advantageously from 45% to 70%, particularly by 60%, with noncharged residues leading to a reduction of positive charges in comparison to the same nonsubstituted polymeric conjugate, facilitating the release of nucleic acid by dissociation of the complex, — the aforementioned residues possess in addition the following properties:

→ they contain at least one hydroxyl group,

→ they do not correspond to a recognition signal recognized by a cellular membrane receptor, — the free $NH_3^+$ functions of the aforementioned components and/or the hydroxyl groups of the aforementioned residues may also be substituted with at least one molecule which constitutes a recognition signal recognized by a cellular membrane receptor, under the condition that the polymeric conjugate contains at least 30% free $NH_3^+$ functions.

In accordance with an advantageous embodiment, the invention concerns a complex between at least one negatively charged nucleic acid and at least one positively charged polymeric conjugate, the association between the nucleic acid and the polymeric conjugate being electrostatic in nature, the polymeric conjugate containing a polymer formed by monomeric components having free $NH_3^+$ functions of the aforementioned components and being as follows:

— the free $NH_3^+$ functions of the aforementioned components are substituted in a ratio of at least 10%, advantageously by 45% to 70%, particularly by 60%, by noncharged residues leading to a reduction of positive charges in comparison to the same nonsubstituted polymeric conjugate, facilitating the release of nucleic acid by dissociation of the complex, — the aforementioned residues possess in addition the following properties:

→ they contain at least one hydroxyl group,

→ they do not correspond to a recognition signal recognized by a cellular membrane receptor, — the hydroxyl groups of the aforementioned residues may also be substituted by at least one molecule which constitutes a recognition signal recognized by a cellular membrane receptor, under the condition that the polymeric conjugate contains at least 30% free $NH_3^+$ functions.

The invention also concerns a positively charged polymeric conjugate, containing components which carry free $NH_3^+$ functions, particularly lysine residues, and being as follows:

— the free $NH_3^+$ functions of the aforementioned components are substituted in a ratio of at least 10%, advantageously by 45% to 70%, by non-charged residues leading to a reduction of positive charges in comparison to the same non-substituted polymeric conjugate, — the aforementioned residues possess in addition the following properties:

→ they contain at least one hydroxyl group,

→ they do not correspond to a cell recognition signal,

— the free $NH_3^+$ functions of the aforementioned components may also be substituted by a molecule which constitutes a cellular membrane recognition signal, this recognition signal having a molecular mass lower than 5,000, and when it is present, this recognition signal can exist at the ratio of one molecule for approximately 10,000 monomer components of the polymeric conjugate or approximately 60 molecules for approximately 10,000 monomer components of the polymeric conjugate.

An advantageous class of polymeric conjugates of the invention contains a polymeric group of the following formula:

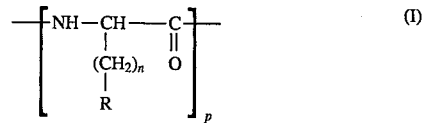

in which:

— p is an integer varying from 2 to 500, preferably from 150 to 200,

— n is an integer varying from 1 and 5 and being preferably 4,

— this polymeric group contains a number of p of R residues among which:

* 10% to 70% of the number of R residues represents a $NH-CO-(CHOH)_m-R_1$ group, particularly a dihydroxylpropionoyle, erythrononoyle, threonoyle, ribonoyle, arabinoyle, xylonoyle, lyxonoyle, gluconoyle, galactonoyle, mannonoyle, glycoheptonoyle, glycooctonoyle residue, — m is an integer from 2 and 15, preferably from 2 to 7, —$R_1$ represents H or an alkyl radical from 1 to 15 carbon atoms, particularly $CH_3$,

* the remaining residues, which are the 30% to 90% of the number of R residues, represent $NH_3^+$,

* R, moreover, having the ability to be constituted in 0 to 25% of the cases by a molecule which constitutes a recognition signal, under the condition that the polymeric conjugate contains at least 30% free $NH_3^+$ functions, and particularly at the ratio of 0.5 to 5, advantageously at 1 molecule for approximately 10,000 components, or at the ratio of 10 to 100, advantageously at 60 molecules for approximately 10,000 components.

Another advantageous class of polymeric conjugates according to the invention contains a polymeric group of formula (II):

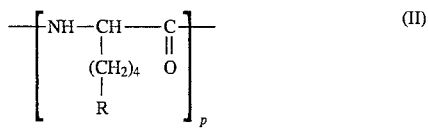

in which p has the meanings indicated above,

* 10% to 70% of the number of R residues represents a $NH-CO-(CHOH)_m-R_1$ group, m and $R_1$ having the meanings indicated above,

* the remaining residues, which are the 30% to 90% of the number of R residues, represent $NH_3^+$.

Another advantageous class of polymeric conjugates according to the invention contains a polymeric group of formula (II):

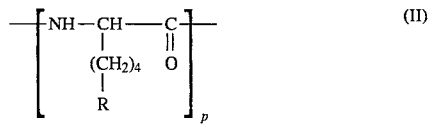

in which:

— p has the meanings indicated above,

— this polymer contains a number p of R residues among which:

* 10% to 70% of the number of R residues represents a $NH-CO-(CHOH)_m-R_1$ group, m and $R_1$ having the meanings indicated above,

* the remaining residues, which are the 30% to 90% of the number of R residues, represent in one part $NH_3^+$ and, in another part, represent a molecule which constitutes a recognition signal at the ratio of 0.5 to 5, advantageously at 1 molecule for 10,000 components.

Another advantageous class of polymeric conjugates according to the invention contains a polymeric group formula (II):

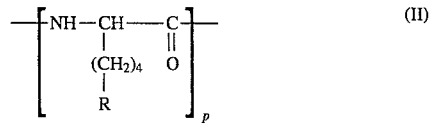

in which:

—p has the meanings indicated above,

—this polymer contains a number p of R residues among which:

* 10% to 70% of the number of R residues represents a $NH-CO-(CHOH)_m-R_1$ group, m and $R_1$ having the meanings indicated above,

* the remaining residues, which are the 30% to 90% of the number of R residues, represent in one part $NH_3^+$ and, in another part, represent a molecule which constitutes a recognition signal at the ratio of 10 to 100, advantageously at 60 molecules for approximately 10,000 components.

In the polymeric conjugates of the invention, the cellular membrane recognition signal could be chosen from those which were clarified for the complexes described above.

The invention also refers to a process of preparation of the complexes described above.

In general terms, a polymer comprising primary amines (free $NH_3^+$ functions) is partially substituted by the reaction with an organic hydroxylated acid (in particular, gluconoic acid), in organic medium.

For example, a polylysine salt (particularly in the form of p-toluene sulfonate) is dissolved in an organic solvent, (particularly dimethylsulfoxide) in the presence of a base (particularly diisopropylethylamine) and treated by an organic hydroxylated activated acid (particularly gluconolactone).

The recognition signals are fixed to the polymer either before or after the introduction of organic hydroxylated acids.

The recognition signals are able to be bound onto e-amino groups of the polymer or onto hydroxyl groups of organic hydroxylated acids; these substitutions follow any of the protocols known by the man skilled in the art.

The nucleic acid/polymer conjugate complex is obtained by mixing a solution of the nucleic acid and a solution of the polymeric conjugate. Preferably, the said solutions are prepared starting from physiologic serum or from a swab ("tampon") or from a cytocompatible medium.

The invention also concerns the use of a complex or of a conjugate according to the invention for the transfection in vitro, ex vivo or in vivo of cells with a gene, particularly those previously defined.

The invention also refers to the use of a complex or a conjugate according to the invention for the transfection of cells which may be chosen from the following:
— cells from hematopoietic strains;
— liver cells;
— cells of skeletal muscles;
— skin cells:
— fibroblasts,
— keratinocytes,
— dendritic cells,
— melanocytes.
— cells of the vascular walls
— endothelial cells
— smooth muscle cells
— epithelial cells of the respiratory tract
— cells of the central nervous system
— cancer cells;
— cells of the immune system, such as lymphocytes, macrophages, NK cells, etc.

A method of in vitro, ex vivo or in vivo transfection in the invention includes the introduction of a complex of the invention into a medium containing cells to be transfected, under conditions such that there exists:
— passage of the complex from the medium into the cytoplasm of the cells,
— release of the nucleic acid of the aforementioned complex into the cytosol of the cells,
— transcription and expression of the nucleic acid into the transfected cells.

The nucleic acid is delivered into the cytosol and/or into the nucleus of the cell to allow gene expression.

The invention also concerns pharmaceutical compositions, including as an active substance at least one of the complexes or at least one of the conjugates according to the invention, in association with an acceptable pharmaceutical vehicle.

The complexes or conjugates of the invention are also able to be a part of a case or a kit, including for example:
— a polymeric conjugate according to the invention, for example, polylysine substituted with a residue leading to a decrease of charges (decrease of the number of the free $NH_3^+$), this polymeric conjugate being possibly substituted with a recognition signal, which beforehand is fixed or not fixed on the polymeric conjugate, the said recognition signal having the function to target the conjugate into selected cells which express a relevant receptor, — possibly a plasmid containing at least one gene to be transferred, and the regulation system of the aforementioned gene, — reagents permitting the possible fixation of the recognition signal on the aforementioned polymeric conjugate, — reagents permitting the formation of a complex according to the invention between the polymeric conjugate and the gene to be transferred, — reagents permitting the transfection of the cell by the aforementioned complex.

Concerning the recognition signal, it should be emphasized that it does not necessarily have to be present on the polymeric conjugate. Indeed, it can be a part of the kit and be bound onto the polymeric conjugate before use. Furthermore, the recognition signal may be absent from the kit and the user can add the recognition signal of his/her choice, according to the cells to be targeted, for the transfer on the polymeric conjugate of the kit.

The invention also concerns the use of a complex or a polymeric conjugate, according to the invention, for the preparation of a medicine to be used, for example, for the treatment of a congenital or acquired metabolic deficiency, for the treatment of tumors, or for the preparation of a vaccine such as a vaccine against the influenza virus.

The polymeric conjugates and the complexes of the invention are suitable to be used to transfect ex vivo all cells suited for antigen presentation, for example, precursors of macrophages, macrophages, B cells or dendritic cells.

When one wishes to transfect macrophages, they can be prepared according to the method described by M. Chokri et al. in *Anticancer Research* 12, 2257–2260, 1992.

The complexes and polymeric conjugates of the invention are suitable to be used for the transfection of macrophages outside of the organism, while in culture environment, before or after separation by elutriation.

One can use a method analogous to that used for the transfection of HepG2 cells, but by using an appropriate oligosaccharide, for example mannose for the mannose receptor (for the transfection of HepG2 cells, one can refer to the examples which follow or to the article by C. Sureau, J. L. Romet-Lemonne, J. Mullins and M. Essex: "Production of hepatitis B virus by a differentiated human hepatoma cell line after transfection with cloned circular HBV DNA." Cell 47, p. 37–47, 1986, or the article by Midoux et al., entitled: "Specific gene transfer mediated by lactosylated poly-L-lysine into hepatoma cells." Nucleic Acids Res., 1993, 21,871–878).

The macrophages transfected "ex vivo" are reinjected into the patient after the verification of the efficacy of the transfection according to the classic methods of immunolabeling.

The nucleic acid in the complex of the invention can be:

— a gene with a therapeutic aim to overcome an inherited or acquired metabolic deficiency (for instance coagulation factors such as factor VIII or factor IX)

— a gene with vaccination purposes (for example a gene encoding either protein expressed on the surface of a tumor, or a virus, bacteria, or parasite protein).

In the case of vaccination by reinjection of transfected macrophages or other antigen presenting cells, the antigenic protein is expressed and is in part presented on the surface of the macrophage, permitting a MHC type 1 dependent antigenic presentation.

The nucleic acid in the complex of the invention is also able to be a gene giving new properties to the macrophages, either directly or by expression of cytokines,

• cytokines having a direct effect on the macrophage, giving it new physiologic properties for example: —transfection of the gene of g interferon; in this case the macrophage is permanently auto-activated, thus augmenting its cytotoxic properties;

— transfection of a modified or unmodified TNFa gene; in this case there is an augmentation of the macrophages' anti-tumoral capacities;

• cytokines having an effect on the cellular population in vicinity of the transfected macrophages;

for example: —transfection of the IL2 gene for the stimulation of the cytotoxic T cells in vicinity of the tumor colonized by the macrophages.

Figure 1:
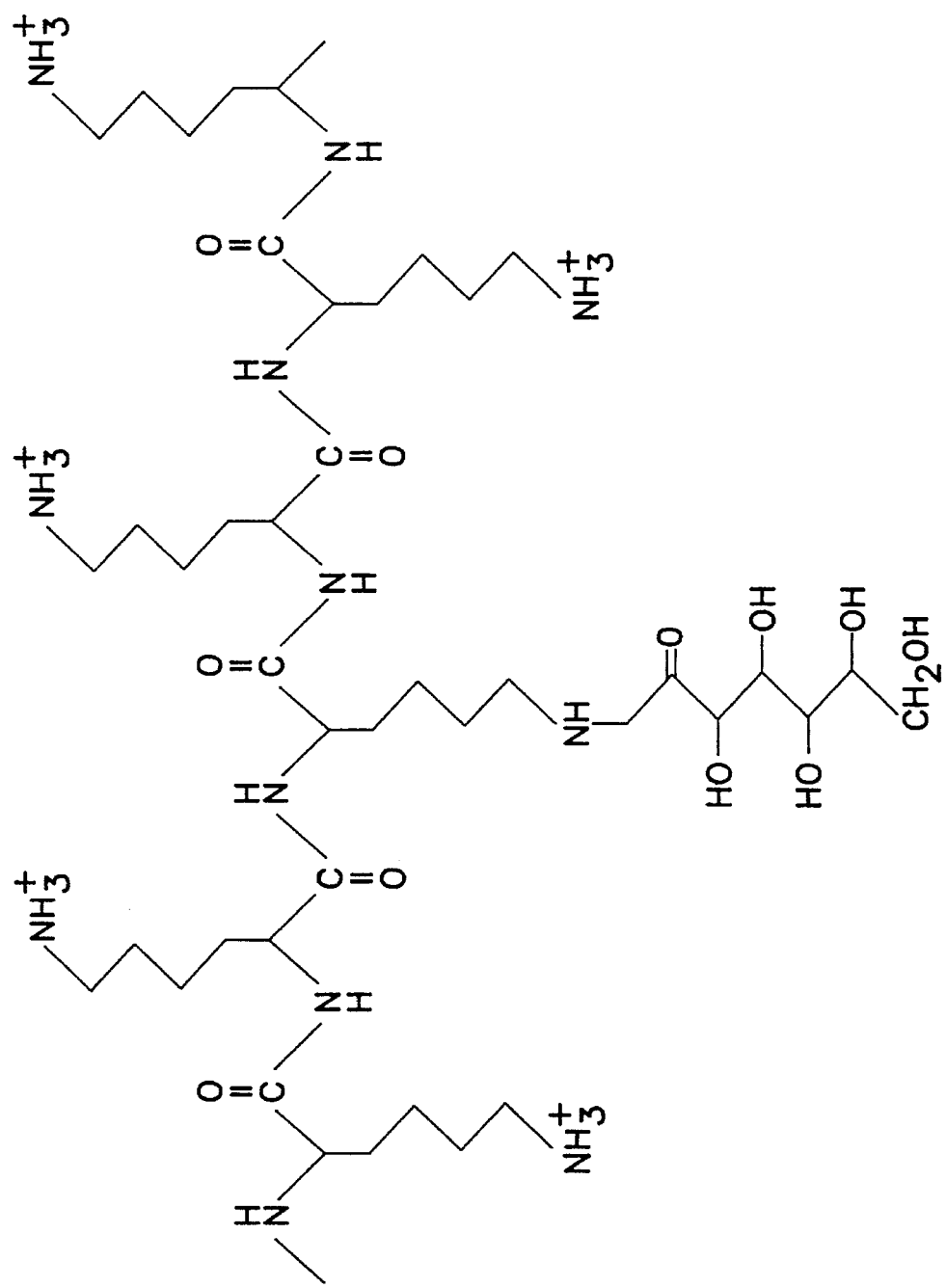
FIG. 1.
Figure 1A:
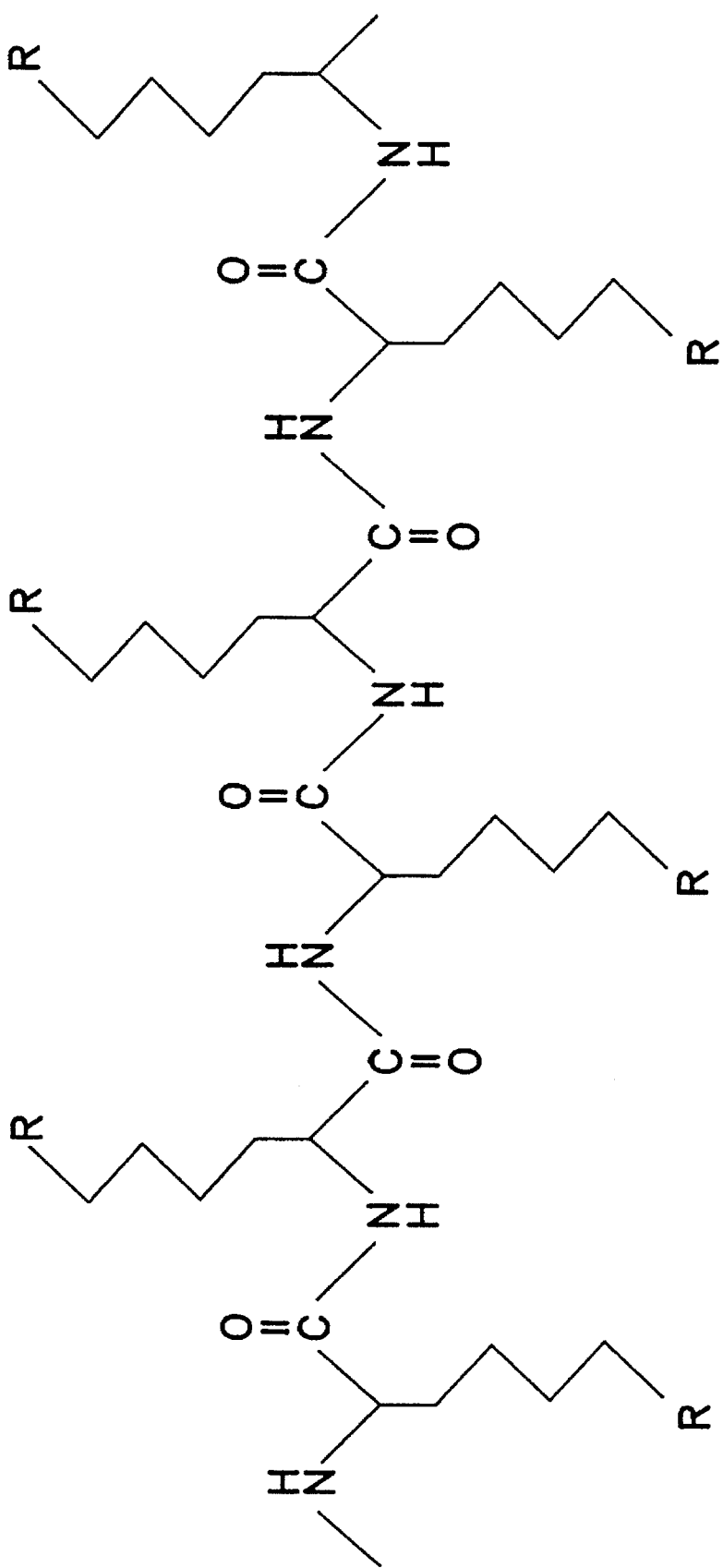
Figure 2:
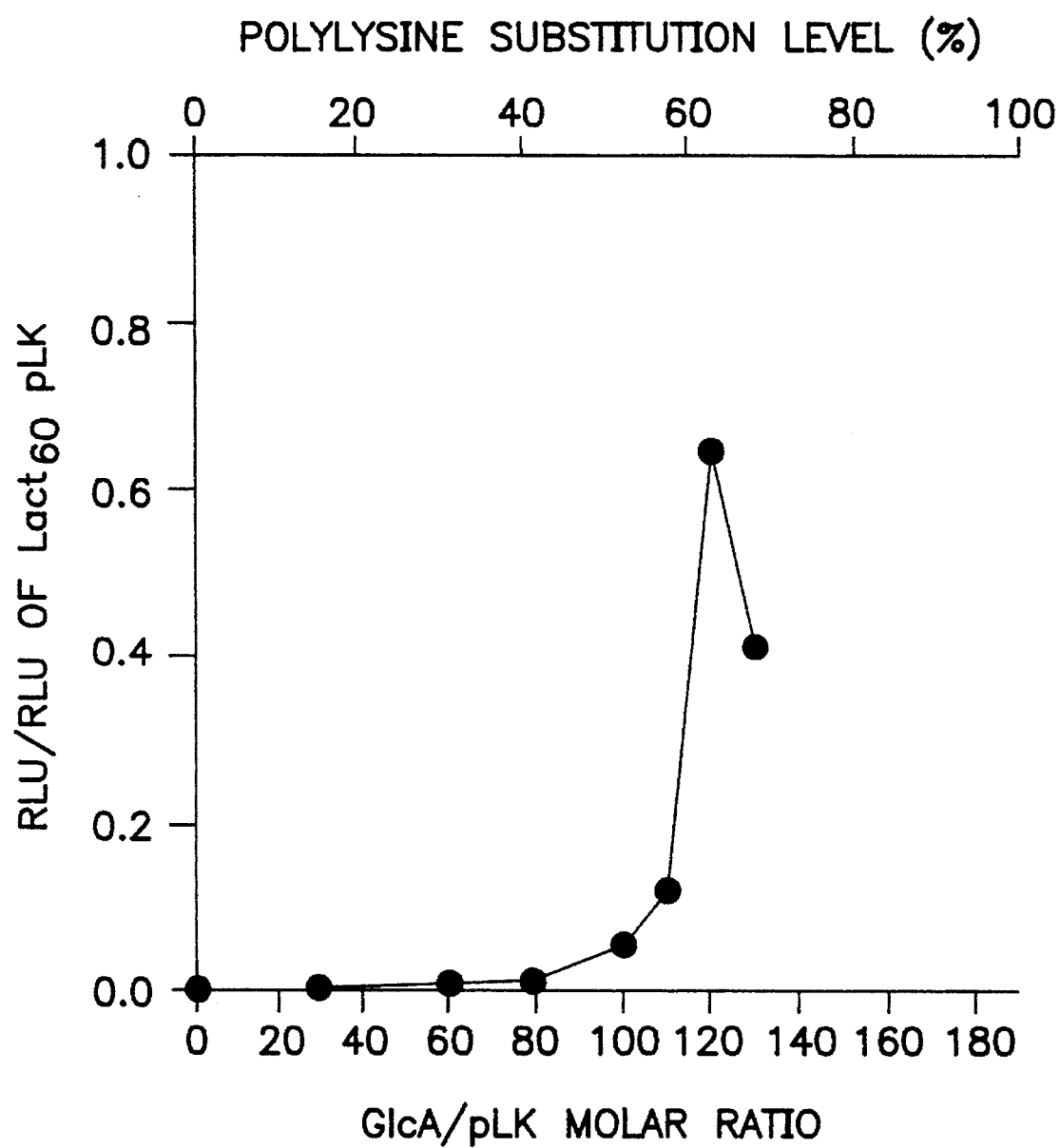

A fragment of gluconoylated polylysine.

FIG. 1a:

A fragment of polylysine in which some of the $NH_3^+$ functions of the polylysine are substituted such that $R=NH_3^+$ or $NNHCO(CHOH)_m R^1$, $R^1$ having the meanings indicated above.

FIG. 2:

Gene transfer in HepG2 cells, using gluconoylated polylysines (GlcA-pLK).

The DNA/polymer complexes formed between the pSV2Luc plasmid and the polylysine substituted by different quantities of gluconoyle residues (from 15 to 70%) have been determined by electrophoresis in agarose gel. The polylysine substituted by more than 140 gluconoyle residues is not able to form a complex with a plasmid stable enough.

The HepG2 cells were incubated at 37° C. for 4 hours in the presence of 100 mM of chloroquine with 1.5 nM of plasmid complexed with each conjugate. The medium was discarded and the cells were further incubated in the absence of both chloroquine and plasmid. Expression of the gene of luciferase was determined 48 hours later by measuring the activity of luciferase in the cellular lysates. The relative light units (RLU) emitted were expressed per mg of protein which corresponds to 1.2 million of HepG2 cells, as a function of the molar ratio GlcA/pLK and of the degree of substitution of polylysine (%).

FIG. 3:

Gene transfer into the HepG2 cells using gluconoylated polylysine (GlcA-pLK).

The DNA/polymer complexes formed between the pSV2Luc plasmid and the polylysine substituted by different quantities of gluconoyle residues (from 15 to 70%) were determined by electrophoresis on agarose gel. The polylysine substituted by more than 140 gluconoyle residues is not able to form a complex with the plasmid stable enough. The HepG2 cells were incubated at 37° C. for 4 hours in presence of 100 mM of chloroquine with 1.5 nM of plasmid complexed with each conjugate. The medium was discarded and the cells were incubated in the absence of both chloroquine and plasmid. Expression of the gene of luciferase was determined 48 hours later by measuring the activity of luciferase in the cellular lysates. The relative light units (RLU) emitted were expressed in relation to those obtained in the same experiment where the transfection of HepG2 cells was with the lactosylated polylysine conjugate ($Lact_{60}pLK$). In graph form, we represented the RLU/RLU values of the $Lact_{60}pLK$ as a function of the molar ratio GlcA/pLK in one part, and by degree of substitution by polylysine (%).

FIG. 3a:

The figure concerns the influence of the number of lactose residues.

The optimal activity of a polymeric conjugate (polymer substituted by lactoses) appears when 30% of the $NH_3^+$ groups are substituted by lactose.

FIG. 4:

The figure concerns gene transfer in different cells using gluconoylated polylysine (GlcA-pLK) using pSV2Luc plasmid.

A DNA/polymer complex was formed between the pSV2Luc plasmid and the polylysine substituted by 120 gluconoyle residues. The cells were incubated at 37° C. for 4 hours in the presence of 100 mM of chloroquine with 1.5 nM of plasmid complexed with the gluconoylated polylysine.

The medium was discarded and the cells were incubated in the absence of both chloroquine and plasmid. Expression of the gene of luciferase was determined 48 hours later by measuring the activity of luciferase in the cellular lysates. The relative light units (RLU) emitted were expressed per mg of protein. Macroll=human macrophages derived from monocytes; RBE4 =rat brain endothelial cells; HEL=leukemic cells of the erythroid lineage.

FIG. 5:

Gene transfer in different cells using gluconoylated polylysine (GlcA-pLK) using CMVLuc plasmid.

A DNA/polymer complex was formed between the CMV-Luc plasmid and the polylysine substituted by 120 gluconoyle residues. The cells were incubated at 37° C. for 4 hours in the presence of 100 mM of chloroquine with 1.5 nM of plasmid complexed with gluconolated polylysine. The medium was discarded and the cells were incubated in the absence of both chloroquine and plasmid. Expression of the gene of luciferase was determined 48 hours later by measuring the activity of luciferase in the cellular lysates. The relative light units (RLU) emitted were expressed per mg of protein. 3LL =cells (mouse) of Lewis lung carcinoma; Macroll=human macrophages derived from monocytes; RBE4=rat brain endothelial cells; HepG2—human hepatocarcinoma; HEL =leukemic cells of the erythroid lineage; K562=another leukemic cell of the erythroid lineage.

FIG. 6:

The figure concerns the measure of the dissociation of the complexes formed between the pSV2Luc plasmid and the polylysine (degree of polymerization=190) substituted with lactose.

Complexes were formed between the pSV2Luc plasmid with either the polylysine (pLK), the polylysine substituted by 60 residues of lactose ($Lact_{60}pLK$), or polylysine substituted by 80 residues of lactose ($Lact_{80}pLK$). The compleses were formed in a solution of 0.15 M NaCl; the concentration of NaCl was then increased. The solutions of DNA/polymer complexes at different concentrations in NaCl were filtered through a 0.45 mm nitrocellulose membrane. In this experiment, the DNA non-complexed to the polylysine passes through the filter while the complexed DNA is retained by the filter. The quantity of DNA dissociated from the polylysine was determined by measuring the quantity of DNA present in the filtrates using DAPI (4',5-diamino-2-phenylindole), (lem =450 nm; lexc=360 nm) (Sigma)) as fluorescent probe. We graphed the percentage of bound DNA/free DNA ratio as a function of the concentration of NaCl (M). O corresponds to pLK, ● corresponds to $pLK,-Lact_{60}$, and V corresponds to pLK,-Lact80.

FIG. 7:

The figure concerns the measure of the solubility of the complexes.

Complexes of DNA/polymer were formed in a solution of 0.15 M NaCl between the pSV2Luc plasmid with either the polylysine (pLK), the gluconoylated polylysine ($GlcA_{120}pLK$), or with polylysine substituted by 60 residues of lactose ($Lact_{60}pLK$). After 30 minutes at 20° C., the absorbency at 610 nm of the solutions was measured.

TABLE 1

Transfection of HepG2 cells by lactolysated and gluconoylated polylysine.

| $RLU \times 10^{-3}$/mg of protein | 5.2 | 19 | 671 | 650 |
|---|---|---|---|---|
| Lact/pLK | 0 | 30 | 30 | 60 |
| GlcA/pLK | 0 | 0 | 30 | 0 |

HepG2 cells were incubated at 37° C. in the presence of 100 mM of chloroquine and 1.5 nM of plasmid complexed with each of the conjugates. After 4 hours, the medium was discarded and the cells were incubated in the absence of both chloroquine and plasmid. Expression of the gene of luciferase was determined 48 hours later by measuring the activity of luciferase in the cellular lysates. The relative light units (RLU) emitted were expressed per mg of protein which corresponds to 1.2 million cells of HepG2. Lact/pLK is the number of lactose molecules per polylysine molecule, and GlcA/pLK is the number of gluconoyle molecules per polylysine molecule.

TABLE II

Transfection of HepG2 cells by bygluconoylated and biotinylated polylysine.

|  | RLU /mg of protein |
|---|---|
| DNA/GlcA, Bio-pLK/Strep/Bio-LactBSA | 966 000 |
| DNA/GlcA, Bio-pLK/Strep/Bio-BSA | 248 000 |
| DNA/GlcA, Bio-pLK/Strep | 237 000 |
| DNA/GlcA, Bio-pLK | 67 000 |
| DNA | 200 |

HepG2 cells were incubated at 37° C. in presence of 100 mM of chloroquine with 1.5 nM of free plasmid or plasmid complexed with each of the conjugates. After 4 hours, the medium was discarded and the cells were incubated in the absence of both chloroquine and plasmid. Expression of the gene of luciferase was determined 48 hours later by measuring the activity of luciferase in the cellular lysates. The relative light units (RLU) emitted were expressed per mg of protein which corresponds to 1.2 million cells of HepG2. GlcA,Bio-pLK=polylysine substituted by 60 gluconoyles and 2.5 biotins; Strep =streptavidin; Bio-LactBSA =lactolysated and biotinylated albumin serum; Bio-BSA=biotinylated albumin serum.

Chemical Components

Luciferine, chloroquine, Triton X 100 and bicinchoninic acid from Sigma (St. Louis, Mo. U.S.A.); L-glutamin, dimethylsulfoxide ($Me_2SO$), ATP, glycerol and $MgCl_2$ from Merck (Darmstadt, Germany); dithiothreitol and D-gluconolactone from Serva (Heidelberg, Germany); diisopropylethylamine, sulfonic p-toluene acid, EDTA from Aldrich (Strasbourg, France); Dowex 2×8, (diameter 0.3–0.9 mm) from Bio-Rad (Richmond, Calif. U.S.A.); 4-isothiocyanatophenyl-b-D-lactoside, 4-isothiocyanatophenyl-b-D-galactopyranoside were prepared as previously described (Monsigny M., Roche A.C. and Midoux P., Uptake of neoglycoproteins via membrane lectins of L 1210 cells evidenced by quantitative flow cytofluorometry and drug targeting. *Biol. Cell.*, 1984: 51: 187–96);the poly-L-lysine, Hbr (30 000–50 000, average molecular mass=40 000, polymerisation degree=190) comes from Bachera Feinchemikalien (Bubendorf, Switzerland). The poly-L-lysine, HBr (1 g in 200 ml of $H_2O$) is passed through an anion exchange column (Dowex 2×8, in OH— form, 0.3–0.9 mm diameter, 35×2.5 cm) in order to take away the bromure (Derrien D., Midoux P., Petit C., Negre E., Mayer R., Monsigny M, and Roche A. C., Muramyl dipeptide bound to poly-L-lysine substituted with mannose and gluconoyle residues as macrophage activators. Glycoconjugate J., 1989: 6: 241–55) which is very cytotoxic for the cells (Weiss S. J., Test S. T., Eckmann C. M., Roos D., and Regiani S., Brominating oxidants generated by human eosinophils. *Science*, 1986: 234: 200–202). The effluent solution is neutralized with 10% p-toluene sulfonic acid in water (a non-cytotoxic compound) and lyophilisated. The lactolysated bovine albumin serum (Lact-BSA, comprised of a mean number of 39 lactose residues) is prepared as previously described (Roche A. C., Barzilay M., Midoux P., Junqua S., Sharon N., and Monsigny M., Sugar-specific endocytosis of glycoproteins by Lewis lung carcinoma cells. *J. Cell. Biochem.*, 1983: 22: 131–40; Monsigny M., Roche A. C., and Midoux P., Uptake of neoglycoproteins via membrane lectin(s) of L 1210 cells evidenced by quantitative flow cytofluorometry and drug targeting. *Biol. Cell.*, 1984: 51: 187–96).

Preparation of the gluconoylated polylysine

The poly-L-lysine in hydromide form, pLK,HBr 30,000–50,000 (molecular mass average=40,000; mean degree of polymerization=190) from Bachem Feinchemikalien (Bubendorf, Switzerland). The polylysine, HBr (1 g in 200 ml $H_2O$) is passed through an anion exchange column (Dowex 2×8, in OH⁻ form, 35×2.5 cm) in order to take away the bromide which is toxic for the cells. The polylysine solution is neutralized with a solution of sulfonic p-toluene acid at 10% in water then lyophilisated.

The polylysine is partially substituted with gluconoyle residues (GlcA) as follows: the polylysine in p-toluene sulfonate form (50 mg; 0.86 mmoles) dissolved in 3 ml of DMSO (dimethylsufoxide) in the presence of diisopropylethylamine (37 ml; 205 mmoles) and 1% of water, is allowed to react for 24 h at 20° C. with quantities of D-gluconolactone ranging from 11 mg (61 mmol) to 35 mg (194 mmol). The gluconoylated polylysine is precipitated by adding 10 volumes of isopropanol. After centrifugation (1,800 g ×15 min), the pellet is washed with isopropanol and collected after another centrifugation. The pellet is dissolved in bidistilated water and the solution is lyophilisated. The mean number of fixed gluconoylated residues per molecule of polylysine, determined by measuring the mean number of free $\epsilon-NH_2$ lysine residues remaining on the polylysine by using the TNBS colorimetric method (TNBS=sulfonic 2,4,6-trinitrobenzene acid) (Fields' R., The measurement of amino groups in proteins and peptides. Biochem. J., 1971: 124: 581–90), is found equal to 105±15. The mean molecular mass is 58,000.

Preparation of conjugates of lactolysated gluconoylated polylysine

The polylysines substituted with either 30 lactose residues ($Lact_{30}pLK$) or with 60 lactose residues ($Lact_{60}pLK$) were prepared as previously described (Midoux P., Mendes C., Legrand A., Raimond J., Mayer R., Monsigny M., and Roche A. C. Specific gene transfer mediated by lactosylated poly-L-lysine into hepatoma cells. Nucleic Acids Res., 1993: 21: 871–78). The lactolysated polylysine containing 30 lactose residues (50 mg: 0.745 mmol) is allowed to react for 24 h at 20° C. with the D-gluconolactone (7.6 mg; 43 mmol) in the presence of diisopropylethylamine (24 ml; 200 mmol) and 1% of $H_2O$. The $Lact_{30}$, -GlcA-pLK polymer is precipitated and purified as previously described. The mean number of bound gluconoyle residues per molecule of conjugate is determined by measuring the a-amino groups of the lysine which remains on the polylysine by using the TNBS colorimetric method (Fields R., The measurement of amino groups in proteins and peptides. Biochem. J., 1971: 124: 581–90), is found equal to 30.

Biotinylation of the polylysine and the gluconoylated polylysine

The gluconoylated polylysine (containing 60 gluconoyle residues) is substituted by biotin: the polymer (20 mg; 0.33 mmol) dissolved in 0.5 ml of 0.1 M sodium carbonate buffer, pH 9.0, containing 0.3 M NaCl, is allowed to react for 20 h at 20° C. with 0.93 mg (1.7 mmol) of sulfosuccinimidyl-6-(biotinamido)hexanoate (NHS-LC-biotin, Pierce). The polymer is precipitated by adding 10 volumes of isopropanol. After centrifugation (1,800 g×15 min), the pellet is washed with isopropanol and collected upon another centrifugation. The pellet is dissolved in bidistilated water and the solution is lyophilized. The mean number of biotin fixed residues per molecule of polymer was determined by using the colorimetric method adapted from Green (Green N. M. A spectrophotomatic assay for avidin and biotin based on binding dyes by avidin. *Biochem. J.*, 1965: 94: 23c–24c) by using 2-(4'-hydroxyazobenzene)benzoic acid (HABA) and streptavidin is found equal to 2.5.

Preparation of biotinylated neoglycoproteins

The BSA and the lactosylated BSA (Lact-BSA) (0.23 mmole) dissolved in 5 ml of 0.1 M sodium carbonate buffer, pH 9.0, containing 0.3 M NaCl is allowed to react for 20 h at 20° C. with NHS-LC-biotin (0.65 mg; 1.2 mmol). The conjugates are purified by filtration on Trisacryl GF05 gel (20×2 cm column) (Sepracor, Villeneuve la Garenne, France) in $H_2O$ containing 5% n-butanol, then lyophilisated. The mean number of linked biotin residues per molecule of protein is determined by using a colorimetric method with HABA, adapted from Green (Green N. M. A spectrophotomatic assay for avidin and biotin based on binding dyes by avidin. Biochem. J., 1965: 94: 23c–24c) and are found to be from 1 for BSA and 2 for Lact-BSA. The average molecular masses of BSA and Lact-BSA are 68,000 and 87,200, respectively.

Cells and cell cultures

HepG2 cells (human hepatocarcinoma, ATCC 8065 HB) which possess a membrane lectin recognizing glycoproteins terminated with b-D-galactose residues (Schwartz A. L., Fridovich S. E., Knowles B. B. and Lodish H. F. Characterization of the asialoglycoprotein receptor in a continuous hepatoma line. *J. Biol. Chem.*, 1981: 256: 8878–81), the HEL cells (ATCC TIB 180) and K-562 (ATCC CCL 243) are cultivated respectively in DMEM medium (GIBCO, Reufrewshire, U.K.) and in RPMI 1640 medium supplemented with 10% heat-inactivated fetal bovine serum (GIBCO), 2 mM of L-glutamine (Merck), antibiotics (100 units/ml of penicillin and 100 mg/ml of streptomycin) (Eurobio., Paris, France). The human macrophages derived from blood monocytes are prepared as described in Roche et al., 1985 (Roche A.C., Midoux P., Bouchard P. and Monsigny M. Membrane lectins on human monocytes: maturation-dependent modulation of 6-phosphomannose and mannose receptors. FEBS Letters, 1985: 193: 63–68). 3LL cells are cultivated as described in Roche et al., 1983 (Roche A. C., Barzilay M., Midoux P., Junqua S., Sharon N., and Monsigny M. Sugar-specific endocytosis of glycoproteins by lewis lung carcinoma cells. *J. Cell. Biochem.*, 1983: 22: 131–40). The RBE4 cells given by P. O. Couraud (Hospital Cochin, Paris) were cultivated on collagen in a α-MEM and HamF$_{10}$ medium (50/50, volume; volume) supplemented with 10% heat-inactivated fetal bovine serum, 2 mM of L-glutamine, antibiotics (100 units/ml of penicillin and 100 mg/ml of streptomycin) in the presence of TGFb.

The plasmids

The plasmid pSV2Luc (5.0 kb) was obtained from Dr. A. B. Brasier (Massachusetts General Hospital, Boston) (Brasier A. R., Tate J. E., and Habener J. F. Optimized use of the firefly luciferase assay as a reporter gene in mammalian cell lines. *Biotechniques*, 1989: 7: 1116–23). The plasmid CMVLuc was given by Dr. A. Dautry-Varsat (Institut Pasteur, Paris).

Formation of optimized plasmid/polylysine conjugate complexes

Only the complexes for which no migration of DNA is produced in electrophoresis on agarose gel, thus named optimized complexes of DNA/polymer, are used for the transfection of cells. The molar ratios between the polymer and the DNA necessary for forming optimized pSV2Luc plasmid/polymer complexes are determined by electrophoresis on agarose gel at 0.6%: the complexes are prepared by adding, drop by drop under constant mixing, variable quantities of polylysine conjugates in 60 ml of DMEM, to 2 mg (0.6 pmol) of pSV2Luc plasmid in 140 ml of DMEM. After incubation for 30 minutes at 20° C., 20 ml of each sample is analyzed by electrophoresis on 0.6% agarose gel (containing ethidium bromide for visualizing the DNA) in a Tris borate EDTA buffer (Tris 95 mM, boric acid 89 mM and EDTA 2.5 mM), pH 8.6.

Preparation of DNA/vector complexes

Complexes of pSV2Luc plasmid and polylysine conjugates

Optimized DNA/polymer complexes are prepared by adding, drop by drop under constant agitation, the polylysine or a conjugate of poly-L-lysine (Lact$_{60}$pLK, GlcA$_x$-pLK, 30 <x<130, with Lact$_{30}$pLK, or Lact$_{30}$-GlcA$_{30}$-pLK) in 0.6 ml of DMEM at 20 mg (6 pmol) of pSV2Luc plasmid in 1.4 ml of DMEM. The solution is maintained for 30 minutes at 20° C.

Complexes of pSV2Luc plasmid and pLK-streptavidine-neoglycoprotein

The optimized complexes of pSV2Luc plasmid/biotinylated polylysine are formed by adding, drop by drop under constant mixing, 10 mg (172 pmol) of gluconoylated and biotinylated polylysine (containing 60 gluconoyle residues) in 290 ml of DMEM to 10 mg (3 pmol) of pSV2Luc plasmid in 0.7 ml of DMEM (molecular ratio between the polymer and the DNA close to 57:1). The solution is maintained for 30 minutes at 20° C. The biotinylated neoglycoproteins (Lact-BSA and BSA) (377 pmol) in 0.5 ml of DMEM are then added, with constant stirring, to 1 ml of pSV2Luc plasmid/biotinylated polylysine complex, and then the streptavidin (27.5 mg; 490 pmol) in 0.5 ml of DMEM is added under agitation (molar ratio between the neoglycoprotein and the DNA close to 125:1) and the solution is maintained for 30 minutes at 20° C.

Gene transfer $5 \times 10^5$ HepG2 cells per well are seeded on day 0 on 12 well tissue culture plates, respectively. On day 1, after removing the medium, the solution (2 ml) containing the plasmid/conjugate complex of polylysine supplemented with 1% heat-inactivated bovine fetal serum, and with 100 mM in the chloroquine (Luthman H. and Magnusson G. High efficiently polyoma DNA transfection of chloroquine treated cells. *Nucleic Acids Res.*, 1983: 11:1295–1308), is added to the wells. After 4 hours of incubation at 37° C., the supernatant is removed and 2 ml of fresh DMEM complete medium is added and the cells are then further incubated for 48 h at 37° C.

Luciferase test

The genetic expression of the luciferase is measured by luminescence according to the method described by De Wet et al., 1987 (De Wet J. R., Wood K. V., De Luca M., Helinski D. R. and Subramani S. Firefly luciferase gene: structure and expression in mammalian cells. *Mol. Cell. Biol.*, 1987: 7: 725–37). The culture medium is removed, and the cells are harvested upon incubation at 37° C. in PBS containing 0.2 mg/ml of EDTA and 2.5 mg/ml of trypsine (GIBCO) and washed 3 times with PBS. The homogenization buffer (200 ml; 8 mM MgCl$_2$, 1 mM of dithiothreitol, 1 mM of EDTA, 1% Triton X 100 and 15 % glycerol, 25 mM of Tris-phosphate buffer pH 7.8), is added to the pellet. The suspension is agitated with a vortex and maintained for 10 min at 20° C., and then centrifuged (5 min, 800 g). ATP (95 ml of a 2 mM solution in the homogenization buffer without Triton X 100) is added to 60 ml of the supernatant and the luminescence is registered for 4 seconds by using a luminometer (Lumat LB 9501, Berthold, Wildbach, Germany) upon automatic addition of 150 ml of 167 mM luciferin in water; the measurements are made in triplicate.

Protein dosage

A protein dosage is made for each sample by using the bicinchoninic colorimetric acid method (BCA) (Smith P. K., Krohn R. I., Hermanson G. T., Mallia A. K., Gartner F. H., Provenzano M. D., Fujimoto E. K., Goeke N. M., Olson B. J. and Klenk D. C. Measurement of protein using bicinchoninic acid. *Anal. Biochem.*, 1985: 150: 76–85), adapted by Hill and Straka (Hill H. D. and Straka J. G. Protein determination using bicinchoninic acid in the presence of sulfhydryl reagents. *Anal. Biochem.*, 1988: 170: 203-08) because of the presence of DTT in the homogenization buffer. The measure of the expression of luciferase is expressed as relative light units (RLU) per mg of BSA (free albumin of purified and crystallized fatty acid, A7511, Sigma), 1 mg BSA corresponding to $1.2 \times 10^6$ HepG2 cells.

Results

Gluconoylated polylysine

The poly-L-lysine (average molecular mass of the salt form 40,000; mean degree of polymerization 190) was partially (from 15 to 70%) acylated at the level of e-NH$_2$ function of the lysine by using D-gluconolactone, an agent which enhances the water solubility. The objective is to reduce the number of positive charges on the polylysine and consequently to reduce the electrostatic interactions between the polymer and a plasmid.

In the presence of polylysine, the DNA is strongly compacted by the cooperative interactions between the positive charges of the polylysine and the negative charges of the DNA.

Figure 3:
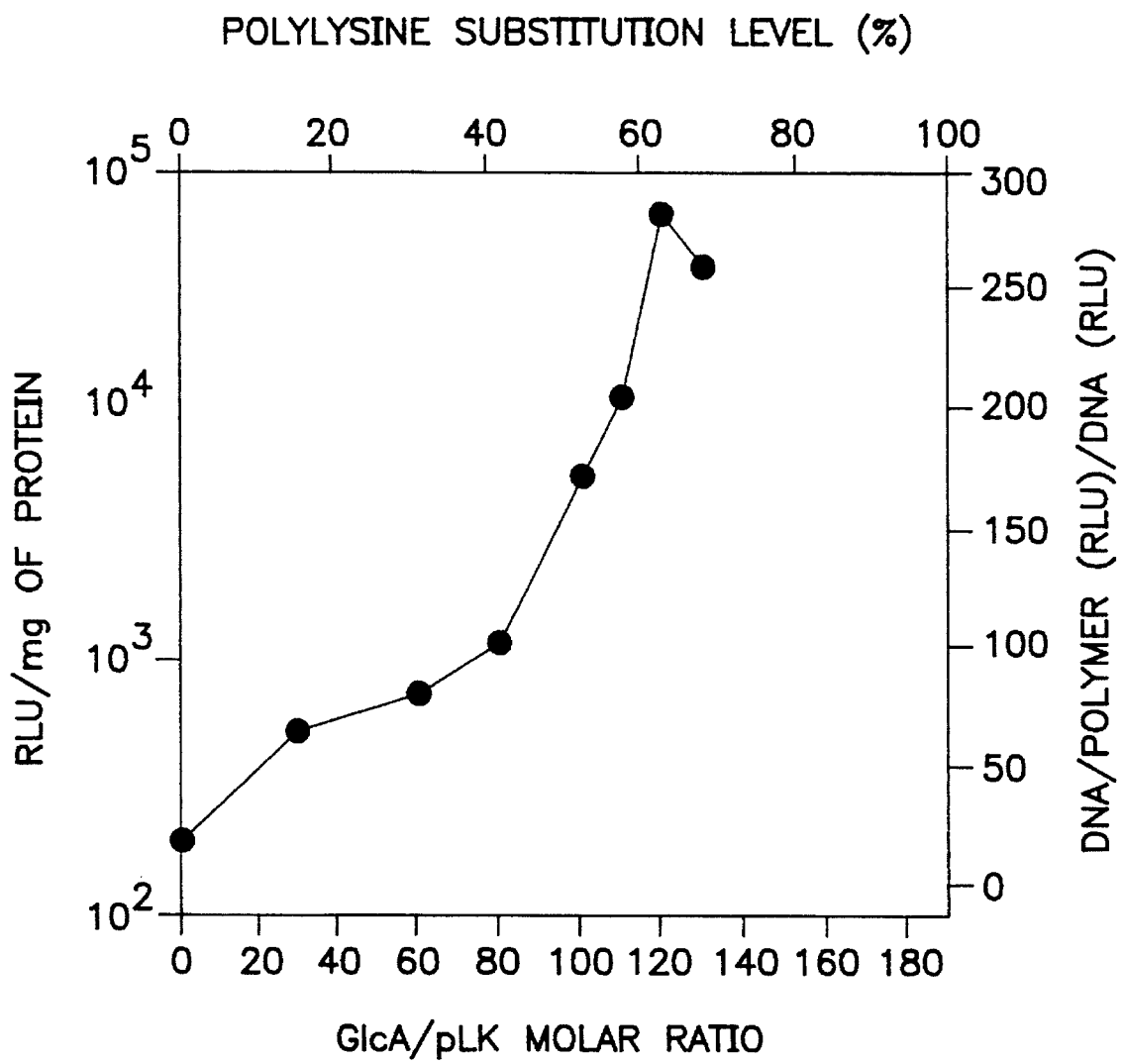
Figure 3A:
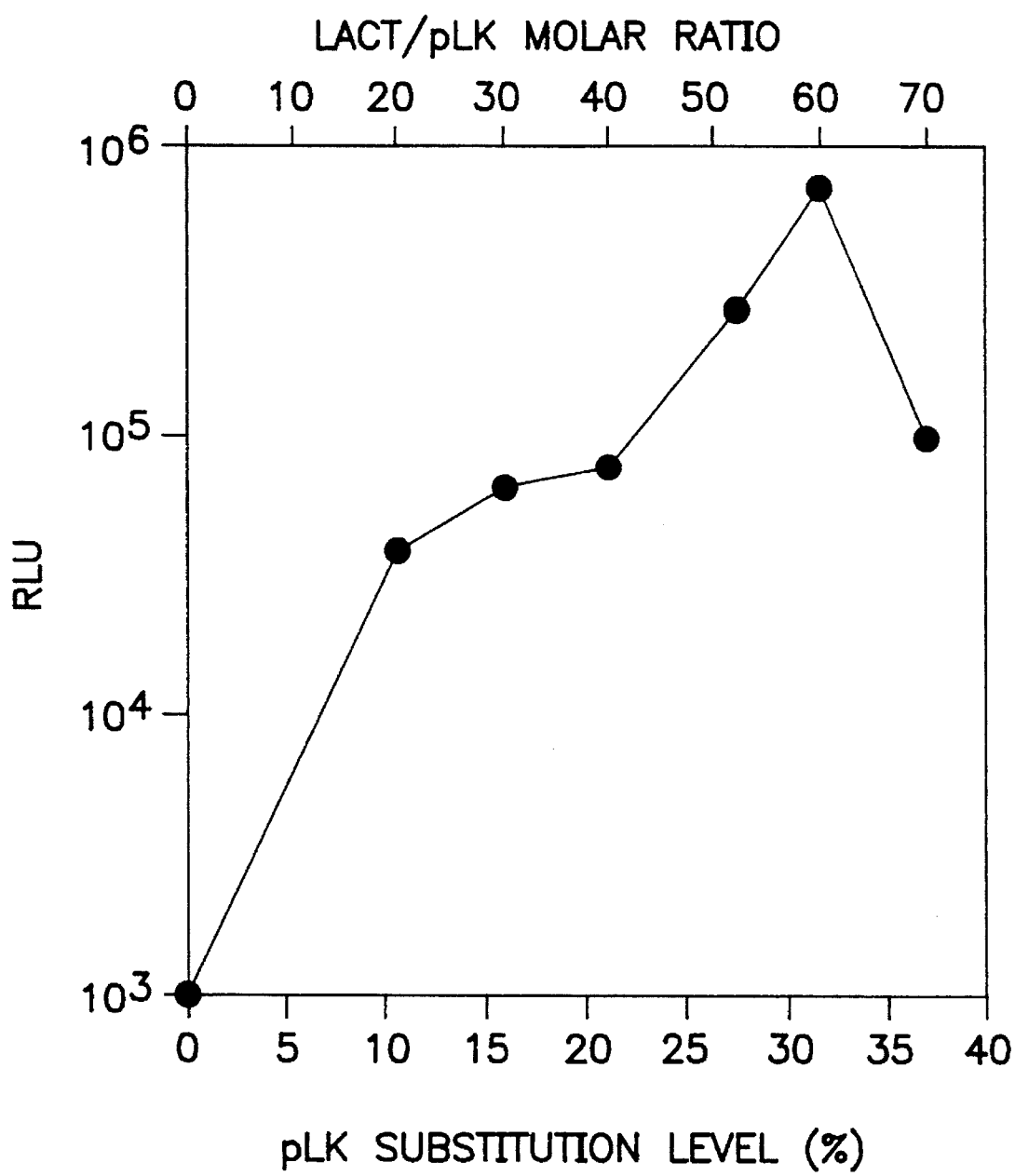

The formation of complexes between a plasmid of 5 kb, such as the pSV2Luc plasmid containing the gene of luciferase with polylysines substituted with increasing quantities of gluconoyle residues, is analyzed by electrophoresis on agarose gel, and the optimized DNA/polymer complexes corresponding to those for which the DNA does not migrate in electrophoresis following the total condensation of the DNA are also readily determined. Above 80% of substitution, the gluconoylated polylysine does not form any complex with DNA As shown in the results of FIG. 3, the increase in expression of the luciferase by the HepG2 cells (human hepatocarcinoma) is related to the increased number of gluconoyle residues fixed on the polylysine and reaching a maximum (approximately 300 times greater than with the plasmid alone) (base line) when the polylysine is substituted with 45 to 70% (88 to 132) gluconoyle residues. The polylysines substituted by few or too many gluconoyle residues are not effective or slightly effective. As a comparison, the expression of the luciferase obtained under the same conditions using lactolysated polylysine under optimal conditions, allows one to conclude that the transfection obtained with the gluconoylated polylysine (substituted at 58%) is comparable to that obtained with the lactosylated polylysine under optimal conditions.

Figure 7:
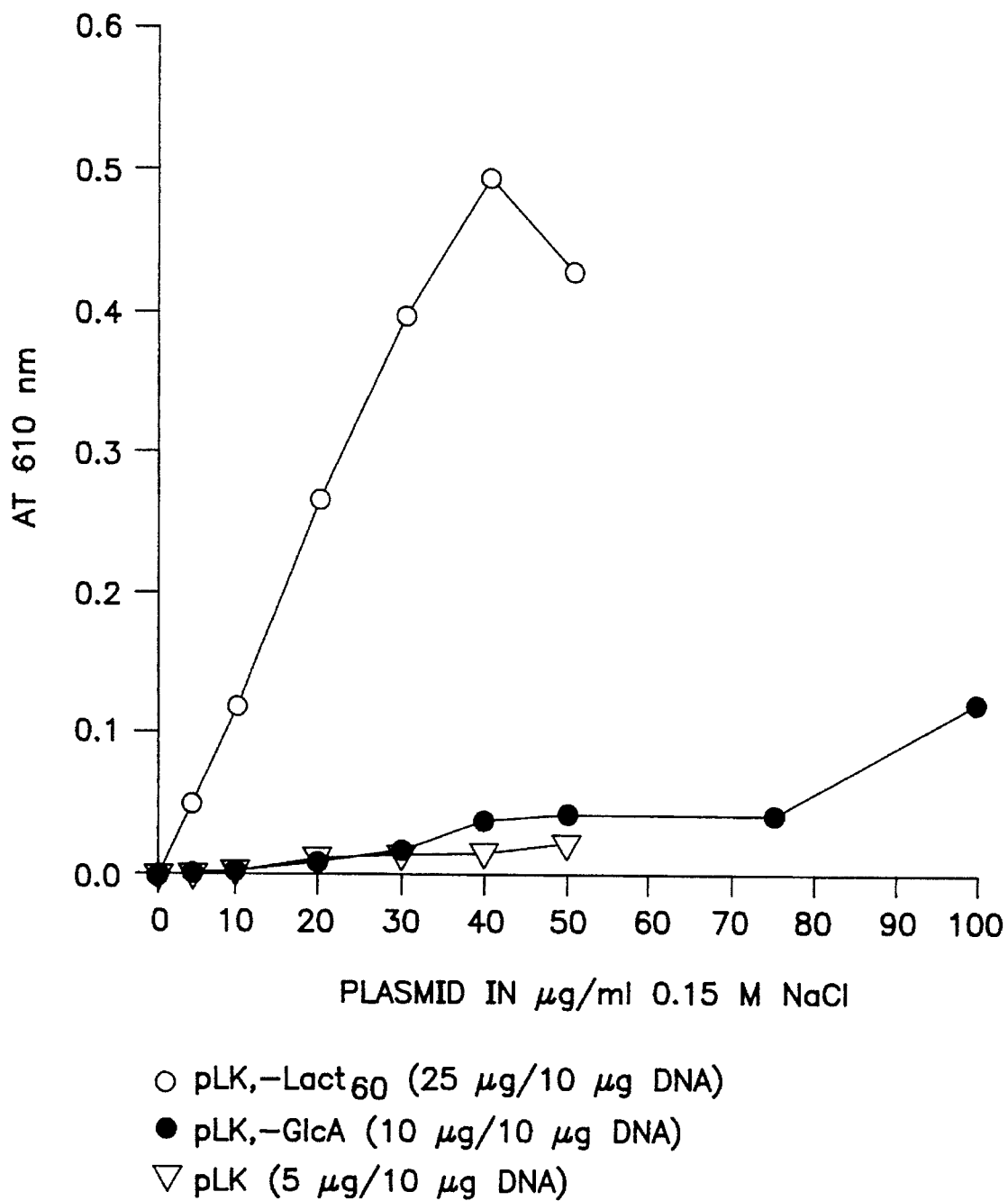

The polylysine substituted by 45 to 70% (88 to 132 residues) of gluconoyle residues allows the preparation of highly concentrated DNA/polymer complexes, up to 100 mg/ml of DNA, while with the lactolysated polylysine, it is only possible to prepare complexes 10 times less concentrated in DNA. FIG. 7 shows, in comparison, the solubility in relation to the concentration of DNA, and of DNA/polylysine, DNA/gluconoylated polylysine and DNA/lactolysated polylysine complexes. This study is monitored by measuring the turbidity (measure of the absorbance at 610 nm) of different solutions. The DNA/polylysine and DNA/gluconoylated polylysine complexes remain soluble up to more than 100 mg/ml, while with the lactolysated polylysine, the complexes precipitate starting from 20 mg/ml. In the presence of polymer, the DNA is strongly compacted as a result of a cooperative phenomenon between the positive and negative charges of the two polymers. In the case of the gluconoylated polylysine, approximately 60% of the positive charges being substituted, the electrostatic interactions between the DNA and the polymer are reduced; this facilitates a dissociation of the DNA/polymer complexes and particularly a release of the DNA in the cell allowing an effective expression of the gene. A study of the modification of the cooperation of electrostatic interactions between the DNA and the gluconoylated polylysine is conducted as a function of the ionic strength and the nature of the counter-ions.

Gluconoylated polylysine furnished with a recognition signal

The gluconoylated polylysine can be substituted by a ligand of low molecular mass such as lactose which has a medium range affinity for a membrane receptor or the biotin which has a very strong affinity for a membrane receptor.

Gluconoylated and lactolysated polylysine

When the polylysine is substituted with 30 lactose residues, the HepG2 cells are very weakly transfected compared to the results obtained with the polylysine substituted with 60 lactose residues (Table 1). The polylysine substituted with 30 lactoses possess more positive charges, interacting strongly with the DNA and impairing a rapid dissociation of the DNA from the complex. When the polylysine containing 30 lactose residues is also substituted with 30 gluconoyle residues, the expression of the luciferase is elevated and comparable to that obtained with the polylysine substituted with 60 lactose residues. The addition of gluconoyle residues permits a reduction of electrostatic interactions between the DNA and the polylysine, facilitating a rapid dissociation of the DNA in the cell.

Gluconoylated and biotinylated polylysine

When the gluconoylated polylysine (containing 60 gluconoyle residues) is substituted by a small number (2.5) of biotin residues, the DNA/biotinylated polylysine complexes have a very strong affinity ($10^{15}$ 1/mole) for the streptavidine. If in addition the streptavidine is furnished with a recognition signal recognized by a membrane receptor specific to a cell type which induces the endocytosis of the complexes, the DNA thus acquires a cellular specificity. This is shown in Table II: the plasmid complexed with gluconoylated and biotinylated polylysine to the streptavidine associated with a recognition signal such as lactolysated serum albumin which is recognized by and taken up via the membrane lectin of HepG2 cells, the expression of the luciferase is much greater than when the albumin serum is lacking lactose or when the streptavidine is lacking a recognition signal.

Gluconoylated polylysine and gene transfer in various cell types

Figure 4:
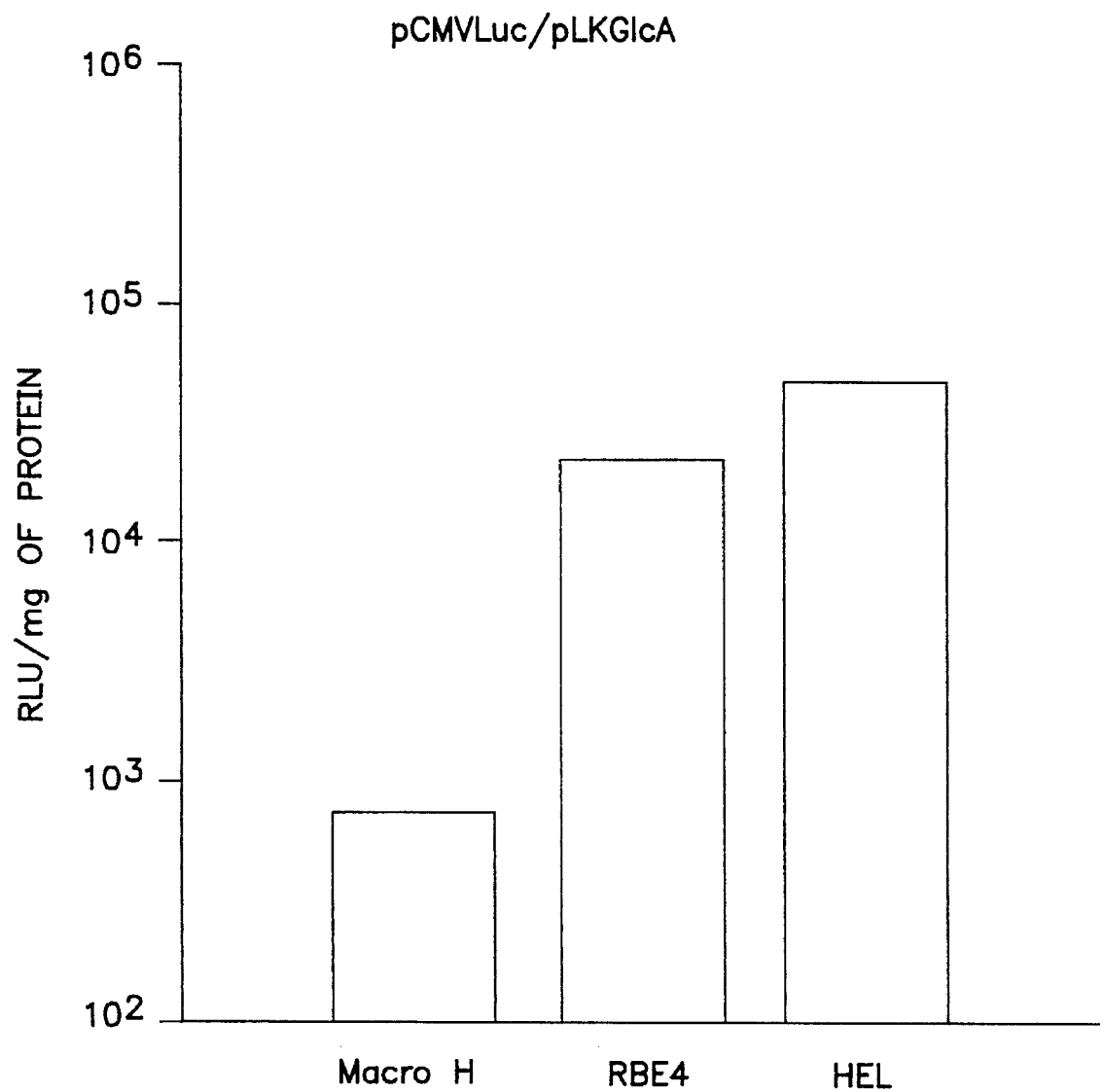
Figure 5:
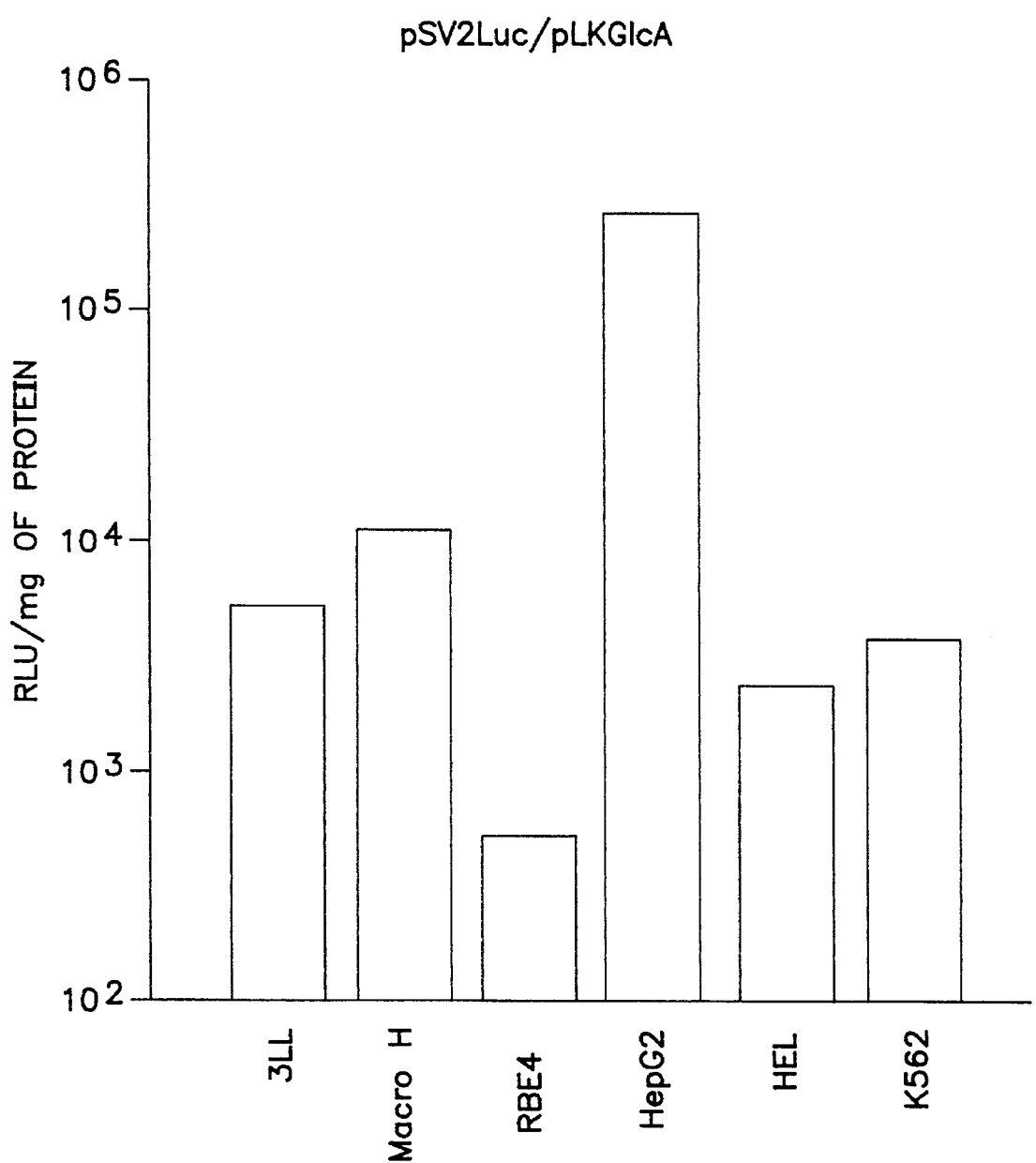
Figure 6:
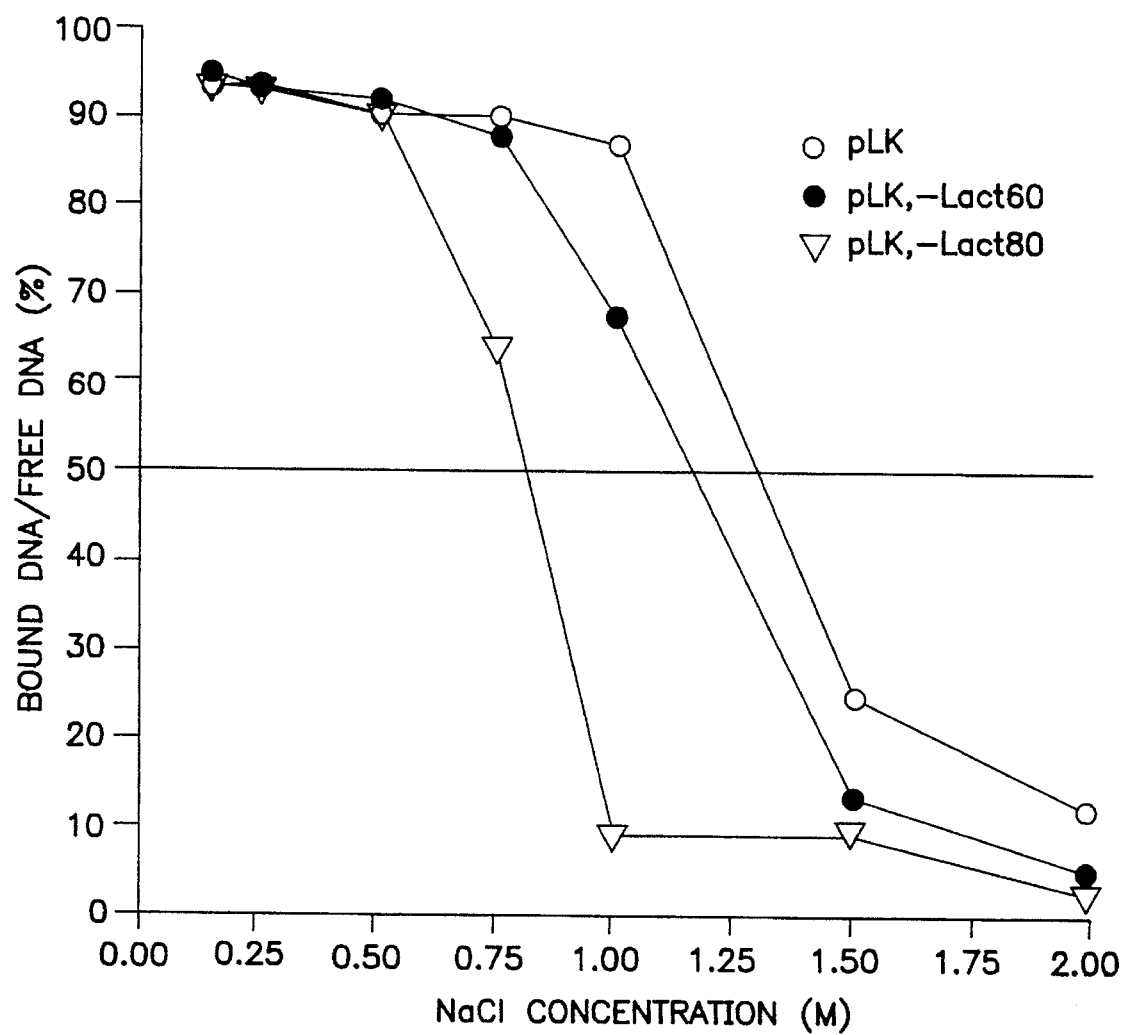

The polylysine substituted with 45 to 70% of gluconoyle residues permits with good efficacy the transfection of adhering cells, such as human macrophages, human hepatocarcinoma, rat endothelial cells, and also of non-adhering cells, such as human T lymphoma and leukemic cells of the erythroid lineage (FIGS. 4 and 5).

Conclusions

The inventive nature of the gluconoylated polylysine lies in:

— the use of a partially substituted polylysine for the reduction of electrostatic interactions between the DNA and the polycationic polymer in order to facilitate the intracellular release of the DNA upon internalization in the cell by a phenomenon of nonspecific endocytosis (the presence of membrane receptors capable of specifically recognizing the gluconoyle residues is not known);

— the gluconoyle residues act also as hydrosolubilizers. and permit the preparation of DNA/polylysine complexes which are highly concentrated and thus better suitable to be used in vivo, which is not the case with the lactolysated polylysine or the polylysine substituted by proteins such as transferrin or asialoorosomucoid;

— the gluconoylated polylysine can be utilized for transfecting various cell types and in particular non-adherent cells;

— the gluconoylated polylysine can be used as a base polymer to confer a cellular specificity to the DNA by the addition of ligand molecules of low molecular mass recognized by specific membrane receptors. The advantage of the gluconoylated polylysine in relation to the non-gluconoylated polylysine is that the former is already optimized for permitting the formation of DNA/polymer-ligand complexes which are easily dissociated in the cell which reduces the number of ligand molecules to be fixed on the polylysine. In fact, it has already been shown that the efficacy of transfection depends on the number of molecules of sugars oses fixed on the non-gluconoylated polylysine (60 lactose residues or 80 galactose residues are necessary for an optimal transfection in the cells possessing a receptor recognized by lactose or galactose).

What we claim is:

1. A compound consisting of polylysine conjugated to noncharged residues wherein the free amino functions of said polylysine are substituted with said non-charged residues, which non-charged residues comprise gluconolactone, and said conjugated polylysine contains at least 30% unsubstituted free amino functions.

2. The compound of claim 1 wherein said non-charged residues further include biotin or lactose.

3. The compound of claim 2 wherein said non-charged residues consist of gluconolactone and biotin.

4. The compound of claim 2 wherein said non-charged residues consist of gluconolactone and lactose.

5. A composition comprising the compound of claim 1 and a nucleic acid.

6. The composition of claim 5 wherein said nucleic acid encodes a genetic marker or a viral antigen.

7. The composition of claim 6 wherein the genetic marker encoded by said nucleic acid is selected from the group consisting of luciferase, β-galactosidase, hygromycin resistance, neomycin resistance, and chloramphenicol acetyl transferase.

8. The composition of claim 6 wherein the viral antigen encoded by said nucleic acid is the nucleoprotein of influenza virus.

9. A method of transfecting cultured cells comprising incubating said cells in the presence of the composition of any one of claims claim 5 through 8 under conditions wherein said composition enters said cells, and the nucleic acid of said composition is released.

* * * * *

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 28
        ( B ) TYPE: Amino Acid
        ( C ) STRANDEDNESS: Unknown
        ( D ) TOPOLOGY: Unknown ( i i ) MOLECULE TYPE: PEPTIDE ( x i ) SEQUENCE DESCRIPTION: SEQ ID NO:1:

```
His  Ser  Asp  Ala  Val  Phe  Thr  Asp  Asn  Tyr  Thr  Arg  Leu  Arg
 1                  5                        10
Lys  Gln  Met  Ala  Val  Lys  Lys  Tyr  Leu  Asn  Ser  Ile  Leu  Asn
15                       20                       25
```

( 2 ) INFORMATION FOR SEQ ID NO: 2:

( i ) SEQUENCE CHARACTERISTICS:
        ( A ) LENGTH: 28
        ( B ) TYPE: Amino Acid
        ( C ) STRANDEDNESS: Unknown
        ( D ) TOPOLOGY: Unknown ( i i ) MOLECULE TYPE: PEPTIDE ( x i ) SEQUENCE DESCRIPTION: SEQ ID NO:2:

```
Ser  Leu  Arg  Arg  Ser  Ser  Cys  Phe  Gly  Gly  Arg  Met  Asp  Arg
 1                  5                        10
Ile  Gly  Ala  Gln  Ser  Gly  Leu  Gly  Cys  Asn  Ser  Phe  Arg  Tyr
15                       20                       25
```

( 2 ) INFORMATION FOR SEQ ID NO: 3:

( i ) SEQUENCE CHARACTERISTICS:
        ( A ) LENGTH: 9
        ( B ) TYPE: Amino Acid
        ( C ) STRANDEDNESS: Unknown
        ( D ) TOPOLOGY: Unknown ( i i ) MOLECULE TYPE: PEPTIDE ( x i ) SEQUENCE DESCRIPTION: SEQ ID NO:3:

```
His  Asp  Met  Asn  Lys  Val  Leu  Asp  Leu
 1                  5
```

( 2 ) INFORMATION FOR SEQ ID NO: 4:

( i ) SEQUENCE CHARACTERISTICS:
        ( A ) LENGTH: 9
        ( B ) TYPE: Amino Acid
        ( C ) STRANDEDNESS: Unknown
        ( D ) TOPOLOGY: Unknown ( i i ) MOLECULE TYPE: PEPTIDE ( x i ) SEQUENCE DESCRIPTION: SEQ ID NO:4:

```
Arg  Pro  Pro  Gly  Phe  Ser  Pro  Phe  Arg
 1                  5
```

( 2 ) INFORMATION FOR SEQ ID NO: 5:

(i) SEQUENCE CHARACTERISTICS:
     (A) LENGTH: 3
     (B) TYPE: Amino Acid
     (C) STRANDEDNESS: Unknown
     (D) TOPOLOGY: Unknown (ii) MOLECULE TYPE: PEPTIDE (xi) SEQUENCE DESCRIPTION: SEQ ID NO:5:

Arg Gly Asp
 1

(2) INFORMATION FOR SEQ ID NO: 6:

(i) SEQUENCE CHARACTERISTICS:
          (A) LENGTH: 3
          (B) TYPE: Amino Acid
          (C) STRANDEDNESS: Unknown
          (D) TOPOLOGY: Unknown (ii) MOLECULE TYPE: PEPTIDES (ix) FEATURE:
          (D) OTHER INFORMATION: The Met at the first
              position is N-formyl-Met (xi) SEQUENCE DESCRIPTION: SEQ ID NO:6:

Met Leu Phe
 1

(2) INFORMATION FOR SEQ ID NO: 7:

(i) SEQUENCE CHARACTERISTICS:
          (A) LENGTH: 13
          (B) TYPE: Amino Acid
          (C) STRANDEDNESS: Unknown
          (D) TOPOLOGY: Unknown (ii) MOLECULE TYPE: PEPTIDE (ix) FEATURE:
          (D) OTHER INFORMATION: The serine in the
              1st position is acetylated (xi) SEQUENCE DESCRIPTION: SEQ ID NO:7:

Ser Tyr Ser Met Glu His Phe Arg Trp Gly Lys Pro Val
 1               5                  10